US008202847B2

(12) United States Patent
Weiner et al.

(10) Patent No.: US 8,202,847 B2
(45) Date of Patent: Jun. 19, 2012

(54) MUTANT HUMAN CD80 AND COMPOSITIONS FOR AND METHODS OF MAKING AND USING THE SAME

(75) Inventors: David B. Weiner, Merion Station, PA (US); Michael G. Agadjanyan, Huntington Beach, CA (US); Rafick P. Sekaly, St. Laurent, CA (US); Mark Holterman, Chicago, IL (US)

(73) Assignees: The Trustees of the University of Pennsylvania, Philadelphia, PA (US); Valorisation-Recherche, Societe En Commandite, Montreal (CA)

( * ) Notice: Subject to any disclaimer, the term of this patent is extended or adjusted under 35 U.S.C. 154(b) by 348 days.

(21) Appl. No.: 12/211,029

(22) Filed: Nov. 10, 2008

(65) Prior Publication Data

US 2011/0002956 A1  Jan. 6, 2011

Related U.S. Application Data

(62) Division of application No. 09/980,762, filed as application No. PCT/US00/11310 on Apr. 27, 2000, now Pat. No. 7,446,189.

(60) Provisional application No. 60/131,764, filed on Apr. 30, 1999.

(51) Int. Cl.
*A61K 31/713* (2006.01)
(52) U.S. Cl. .................................................. 514/44 R
(58) Field of Classification Search .................. None
See application file for complete search history.

(56) References Cited

U.S. PATENT DOCUMENTS

| | | | |
|---|---|---|---|
| 4,722,848 A | 2/1988 | Paoletti et al. |
| 4,736,866 A | 4/1988 | Leder et al. |
| 4,873,191 A | 10/1989 | Wagner et al. |
| 4,945,050 A | 7/1990 | Sanford et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey, III et al. |
| 5,174,993 A | 12/1992 | Paoletti |
| 5,223,424 A | 6/1993 | Cochran et al. |
| 5,225,336 A | 7/1993 | Paoletti et al. |
| 5,240,703 A | 8/1993 | Cochran |
| 5,242,829 A | 9/1993 | Panicali et al. |
| 5,294,441 A | 3/1994 | Curtiss |
| 5,294,548 A | 3/1994 | McLinden et al. |
| 5,310,668 A | 5/1994 | Ellis et al. |
| 5,387,744 A | 2/1995 | Curtiss, III et al. |
| 5,389,368 A | 2/1995 | Curtiss, III |
| 5,424,065 A | 6/1995 | Curtiss, III et al. |
| 5,451,499 A | 9/1995 | Cochran |
| 5,453,364 A | 9/1995 | Paoletti |
| 5,462,734 A | 10/1995 | Letchworth, III et al. |
| 5,470,734 A | 11/1995 | Sondermeijer et al. |
| 5,482,713 A | 1/1996 | Paoletti |
| 5,554,528 A | 9/1996 | Harrison et al. |
| 5,585,268 A | 12/1996 | Knapp et al. |
| 5,589,466 A | 12/1996 | Felgher et al. |
| 5,593,972 A | 1/1997 | Weiner et al. |
| 5,739,118 A | 4/1998 | Carrano et al. |
| 5,830,876 A | 11/1998 | Weiner et al. |
| 5,837,533 A | 11/1998 | Boutin |
| 5,942,607 A | 8/1999 | Freeman et al. |
| 6,248,329 B1 * | 6/2001 | Chandrashekar et al. . 424/191.1 |
| 2004/0157296 A1 | 8/2004 | Yang et al. |

FOREIGN PATENT DOCUMENTS

| | | |
|---|---|---|
| WO | WO9011092 | 10/1990 |
| WO | WO9317706 | 9/1993 |
| WO | WO9323552 | 11/1993 |
| WO | WO9416737 | 8/1994 |
| WO | WO9503408 | 2/1995 |
| WO | WO9526718 | 10/1995 |
| WO | WO9610038 | 4/1996 |
| WO | WO9611279 | 4/1996 |
| WO | WO9640915 | 12/1996 |

OTHER PUBLICATIONS

Singh et al., Nature Biotechnology, 1999, 17: 1075-1081.*
Ezzell, Journal of NIH Research 1995, 7: 46-49.*
International search report for PCT/US00/11310 dated Oct. 17, 2000.
Selvakumar et al., "Genomic Organization and Chromosomal Location of the Human Gene Encoding the B-Lymphocyte Activation Antigen B7," PubMed, 1992, abstract only.
Lanier et al., "CD80 (B7) and CD86 (B70) Provide Similar Costimulatory Signals for T Cell Proliferation, Cytokine Production, and Generation of CTL," PubMed, 1995, abstract only.
Azuma et al., "B70 Antigen is a Second Ligand for CTLA-4 and CD28," Nature, Nov. 4, 1993, vol. 366, pp. 76-79.
Freeman et al., "Structure, Expression, and T Cell Costimulatory Activity of the Murine Homologue of the Human B Lymphocyte Activation Antigen B7," J. Exp. Med., Sep. 1991, vol. 174, pp. 625-631.
Freeman et al., "A New Member of the Ig Superfamily with Unique Expression on Activated and Neoplastic B Cells," The Journal of Immunology, Jul. 11, 1989, vol. 143, pp. 2714-2722. Howell et al., "Limited T-Cell Receptor B-Chain Heterogeneity Among Interleukin 2 Receptor-Positive Synovial T Cells Suggests a Role for Superantigen in Rheumatoid Arthritis," Proc. Natl. Acad Sci., Dec. 1991, vol. 88, pp. 10921-10925.
Kim et al., "Engineering of In Vivo Immune Responses to DNA Immunization Via Codelivery of Costimulatory Molecule Genes," Nature Biotechnology, Jul. 15, 1997, vol. 15, pp. 641-646.
Oksenberg et al., "Limited Heterogeneity of Rearranged T-Cell Receptor Vα Transcripts in Brains of Multiple Sclerois Patients," Letters to Nature, May 24, 1990, vol. 345, pp. 344-346.
Paliard et al., "Evidence for the Effects of a Superantigen in Rheumatoid Arthritis," Science, Jul. 19, 1991, vol. 253, pp. 325-329.
Linsley et al., "Human B7-1 (CD80) and B7-2 (CD86) Bind with Similar Avidities but Distinct Kinetics to CD28 and CTLA-4 Receptors," PubMed, Dec. 1994, vol. 1, No. 9, abstract only.
W. Williams, "Restricted Heterogeneity of T Cell Receptor Transcripts in Rheumatoid Synovium" J. Clin. Invest., Aug. 1992, vol. 90, pp. 326-333.
Chaudhary et al., "A Rapid Method of Cloning Functional Variable-Region Antibody Genes in *Escherichia coli* as Single-Chain Immunotoxins," Proc. Natl. Acad. Sci., Feb. 1990, vol. 87, pp. 1066-1070.

(Continued)

*Primary Examiner* — Ilia Ouspenski
(74) *Attorney, Agent, or Firm* — Petter Hamilton, LLP

(57) ABSTRACT

Improved vaccines and methods of using the same are disclosed Immunosuppressive compositions for treating individuals who have autoimmune diseases or transplants and methods of using the same are disclosed.

21 Claims, 6 Drawing Sheets

OTHER PUBLICATIONS

K. Wucherpfennig, et al., "Shared Human T Cell Receptor Vβ Usage to Immunodominant Regions of Myelin Basic Protein," Science, 1990. vol. 248, pp. 1016-1019.

European Search Report dated Jun. 18, 2008, Application No. 00926416.

Gerstmayer et al., "Costimulation of T-cell Proliferation by a Chimeric B7-Antibody Fusion Protein," Cancer Immunol Immunother, vol. 45, Nos. 3-4, pp. 156-158 (1997).

Fargeas et al., "Idenification of Residues in the V Domain of CD80 (B7-1) Implicated in Functional Interactions with CD28 and CTLA4," Journal of Experimental Medicine, Sep. 1, 1995, Tokyo, JP, vol. 182, pp. 667-675.

Peach et al., "Both Extracellular Immunoglobulin-like Domains of CD80 Contain Residues Critical for Binding T Cell Surface Receptors CTLA-4 and CD28," Journal of Biological Chemistry, vol. 270, No. 36, Sep. 8, 1995, pp. 21181-21187.

Inobe et al., "Identification of an Alternatively Spliced Form of the Murine Homologue of B7," Biochemical and Biophysical Research Communications, vol. 200, No. 1, pp. 443-449, (1994).

Morton et al., "Differential effects of CTLA-4 substitutions on the binding of human CD80 (B7-1) and CD86 (B7-2)," J Immunology (1996) 156:1047-1054.

Lanier et al., "CD80 (B7) and CD86 (B70) provide similar costimulatory signals to T cell proliferation, cytokine production and generation of CTL", J. Immunol. vol. 154, No. 1, Jan. 1, 1995, pp. 97-105.

Linsley et al., "Human B7-1 (CD80) and B&-2 (CD86) bind with similar avidities but distinct kinetics to CD28 and CTLA-4 receptors", Immunity vol. 1, No. 9, Dec. 1994, p. 793-801.

\* cited by examiner

A)

B)

MUTANT HUMAN CD80 AND COMPOSITIONS FOR AND METHODS OF MAKING AND USING THE SAME

CROSS-REFERENCE TO RELATED APPLICATIONS

This application a division of U.S. patent application Ser. No. 09/980,762, filed Sep. 3, 2002, allowed, which is the U.S. National Stage filing of International Application Serial No. PCT/US00/11310 filed Apr. 27, 2000, which claims priority to U.S. Provisional Patent Application No. 60/131,764, filed Apr. 30, 1999, each of which is incorporated herein by reference in its entirety.

FIELD OF THE INVENTION

The present invention relates to compositions for and methods of immunizing individuals, to immunosuppressive compositions, components thereof and methods of making and using the same.

BACKGROUND OF THE INVENTION

This application is related to U.S. Provisional Application Ser. No. 60/131,764 filed Apr. 30, 1999, which is incorporated herein by reference.

CD28 is a cell surface glycoprotein constitutively expressed on most mature T-cells and thymocytes, while the CTLA-4 receptor is not present on resting T cells and is only detectable 48 to 72 hours after T cell activation. The principal ligands for CD28/CTLA-4 molecules are B7.1 (CD80) and B7.2 (CD86) expressed on the surface of professional antigen presenting cells (APC). The biological rationale for the existence of at least two receptors (CD28 and CTLA-4) and two ligands (CD80 and CD86) is not clear. It was initially demonstrated that CD80 and CD86 antigens were functionally similar. However, different roles for these co-stimulatory molecules were first suggested when the different patterns of their expression were determined. CD86 is constitutively expressed on APC and after activation of APC, the expression of CD86 is quickly up-regulated followed by a gradual return to baseline levels. The expression of CD80 is delayed compared to CD86 and its expression is maximal 48 to 72 hours after the initiation of an immune response. Because CD86 expressed constitutively and up-regulated earlier than CD80 it was suggested that CD86 expression is important for the early phase of an immune response, while CD80 is important for the second.

Functional differences between CD80 and CD86 are further suggested by data on the binding kinetics of co-stimulatory molecules with CD28 and CTLA-4. Surface plasmon resonance (SPR) analysis has demonstrated that both ligands bind to CTLA-4 with higher avidity than to CD28. Further measurements revealed that the CD86/CTLA-4 complex dissociates faster than the CD80/CTLA-4 complex. These binding differences combined with the similar delay in expression of CTLA-4 and CD80 suggest that functional relationship between CTLA-4 and CD80 is probably more potent than functional relationship between CTLA-4 and CD86 molecules.

Multiple functions for CD80 and CD86 molecules in vitro and in vivo have been also reported. Anti-CD86 but not anti-CD80 antibodies block the development of disease in a mouse model of autoimmune diabetes, whereas the opposite effect is seen with these antibodies in a murine model of experimental allergic encephalomyelitis. Several experimental systems demonstrate an important role for CD86 in initiating a T-cell response to antigen and that the CD80 molecule may play an important role in providing modulatory signals to these cells. It was observed that expression of exogenous human CD86, but not CD80, provides important activation signals to murine T cells following DNA vaccination with envelope proteins from HIV-1. Similar results were observed after immunization of mice with DNA encoding HIV-1 or influenza antigens and plasmids encoding murine CD80 and CD86. Thus, functional differences between CD80 and CD86 were not connected with differential immunogenicity of human costimulatory molecules expressed in the mouse organism. It is believed that exogenous human or murine CD86, but not CD80, stimulates anti-viral T-cell activation during DNA immunization.

Vaccines are useful to immunize individuals against target antigens such as pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines which produce the target antigen in the cell of the vaccinated individual are effective in inducing the cellular arm of the immune system. Specifically, live attenuated vaccines, recombinant vaccines which use avirulent vectors and DNA vaccines all lead to the production of antigens in the cell of the vaccinated individual which results induction of the cellular arm of the immune system. On the other hand, subunit vaccines, which comprise only proteins, and killed or inactivated vaccines induce humoral responses but do not induce good cellular immune responses.

A cellular immune response is often necessary to provide protection against pathogen infection and to provide effective immune-mediated therapy for treatment of pathogen infection, cancer or autoimmune diseases. Accordingly, vaccines which produce the target antigen in the cell of the vaccinated individual such as live attenuated vaccines, recombinant vaccines which use avirulent vectors and DNA vaccines are often preferred.

While such vaccines are often effective to immunize individuals prophylactically or therapeutically against pathogen infection or human diseases, there is a need for improved vaccines. There is a need for compositions and methods which produce an enhanced immune response.

Gene therapy, in contrast to immunization, uses nucleic acid molecules that encode non-immunogenic proteins whose expression confers a therapeutic benefit to an individual to whom the nucleic acid molecules are administered. A specific type of gene therapy relates to the delivery of genetic material which encodes non-immunogenic proteins that modulate immune responses in the individual and thus confer a therapeutic benefit. For example, protocols can be designed to deliver genetic material which encodes non-immunogenic proteins that downregulate immune responses associated with an autoimmune disease in an individual and thus confer a therapeutic benefit to the individual. There is a need for compositions and methods which can be used in gene therapy protocols to modulate immune responses.

Modulation of immune responses by alternative means is similarly desirable to treat diseases such as autoimmune disease and cell/tissue/organ rejection. There is a need for compositions and methods which can be used to modulate immune responses and to design and discover compositions useful to modulate immune responses.

DESCRIPTION OF PREFERRED EMBODIMENTS OF THE INVENTION

Figure 1:
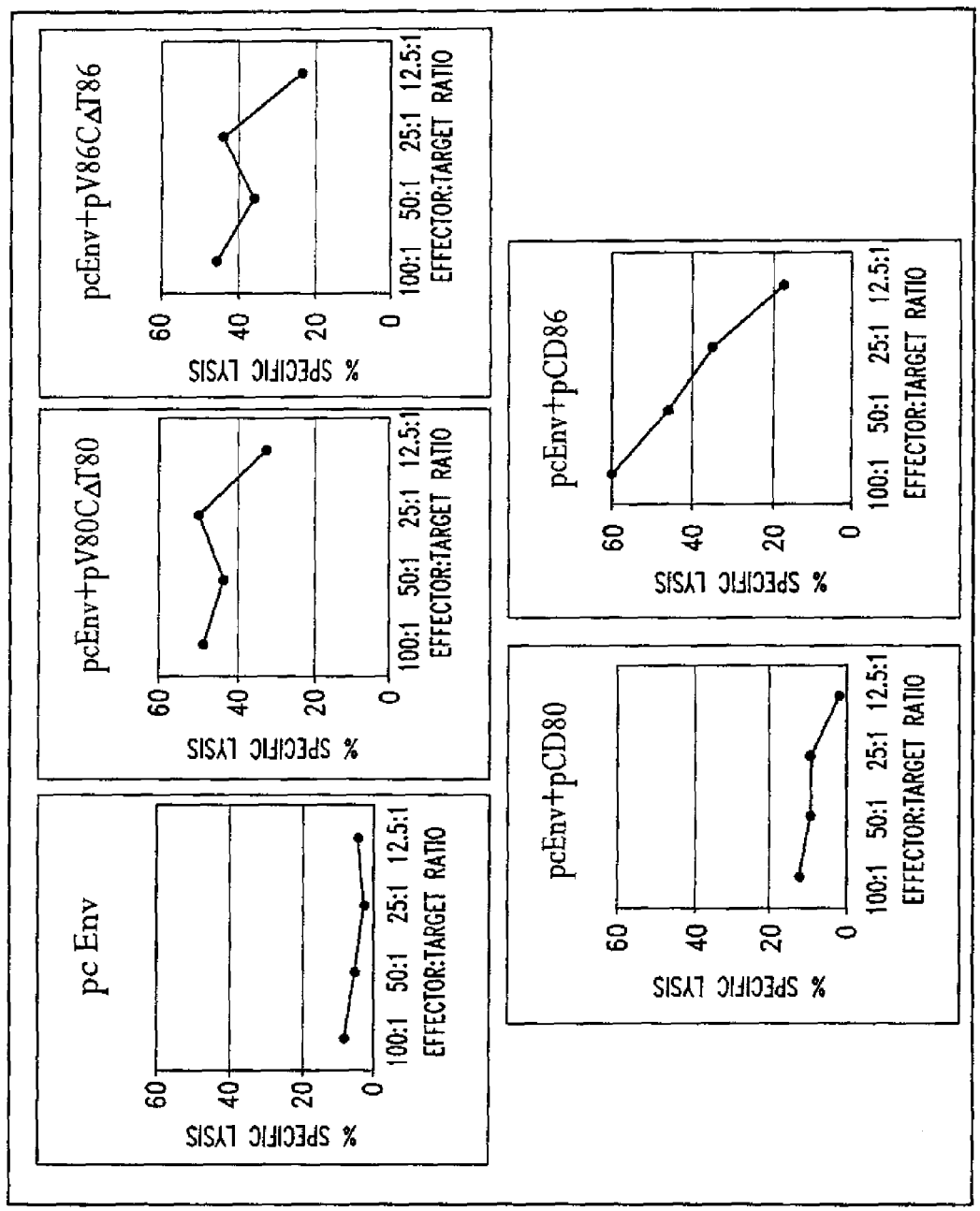
FIG. 1 shows data from experiments described in the Example showing antigen specific anti-viral CTL responses.

Applicants have discovered that the C region of human CD80 is responsible for transmuting a negative signal when an antigen presenting cell (APC) interacts with a T cell. The negative signal results in a reduction in the activity of the T cell and thus a reduction in the immune response generated against the antigen presented by the APC to the T cell. Specifically, the interaction between a T cell receptor (TCR) on a T cell with an MHC/antigen complex that has been formed on an APC by the formation of a complex between a major histocompatibility complex (MHC) protein and an antigen is accompanied by the interaction between the co-stimulatory molecules CD80 and CD86 present on the APC with CD28 molecules on the T cell. Such interaction results in T cell activation and an elevated immune response. However, following T cell activation, CTLA4 is expressed by T cells. CTLA4 interacts with CD80 and such interaction results in a dominant negative signal which eliminates the previous co-stimulatory effect caused by CD80 and CD86 interaction with CD28. The result of CD80 interaction with CTLA4 is a reduction in the immune response with which the T cell is involved.

Applicants discovery provides for two distinct aspects of the invention. According to one aspect of the invention, CD80 mutants and nucleic acids encoding the same are provided which possess the co-stimulatory activity of CD80 but which do not transmute the negative signal associated with CD80 interaction with CTLA4. Such CD80 mutants are useful in immunization protocols in which they are delivered, as proteins or nucleic acids encoding such proteins, together with immunogens which are delivered as protein immunogens or nucleic acid molecules encoding immunogens. The CD80 mutants of this aspect of the invention are molecular adjuvants in immunization protocols. According to another aspect of the invention, CD80 mutants and nucleic acids encoding the same are provided which possess the CD80 C region so that they transmute the negative signal associated with CD80 interaction with CTLA4. Such CD80 mutants are useful in the treatment of autoimmune diseases and immunosuppression protocols associated with cell, tissue and organ transplants. The CD80 mutants which provide the negative signal may be delivered as proteins or nucleic acids encoding such proteins. The CD80 mutants of this aspect of the invention are autoimmune/immunesuppressive therapeutics.

The nucleotide and amino acid sequences of human CD80 is well known and set forth in Freeman et al. (1989) J. Immunol. 143(8):2714-2722, Selvakumar et al. (1992) Immunogenetics 36(3):175-181, Freeman et al. (1991) J. Ex. Med. 174 (3):625-631, Lanier et al. (1989) J. Immunol. 154(1):97-105, and Genbank accession code P33681 (www.ncbi.nlm.nih.gov), which are each incorporated herein by reference.

CD86 (B7.2) was first described in Azuma, M. et al. 1993 Nature 366:76-79, which is incorporated herein by reference. FIG. 2B of that publication discloses the nucleotide and predicted amino acid sequence of the B7.2 protein. The sequence information is also available in the Genbank database as U04343 which is incorporated herein by reference.

Human CD80 is expressed as a 288 amino acid protein (1-288) which is processed to a mature protein (35-288). CD80 is divided into four regions: the variable (V) region, the constant (C) region, the transmembrane region (tm) and the cytoplasmic tail region (et). Amino acids 35-242 make up the extracellular domain of the protein. Amino acids 43-123 make up the V region, also referred to as the Immunoglobulin like V-type domain. Amino acids 155-223 make up the C region, also referred to as the Immunoglobulin like C2-type domain. Amino acids 243-263 make up the transmembrane region. Amino acids 264-288 make up the cytoplasmic tail.

As used herein, the terms "CD80 mutants", "C region CD80 mutants", "C region deficient CD80 mutants" and "CD80ΔC mutants" are used interchangeably and are meant to refer to molecules which contain either a functional CD80 or CD86 V region, at least one functional non-C region of CD80 and which are free of a functional C region of CD80 such that, through the absence of all or part of the C region, such molecules do not transmute the negative signal associated with wild type CD80 C region interactions with CTLA4.

As used herein, references to a "functional region of CD80" as used in the phrases to "at least one functional non-C region of CD80" and "functional C region of CD80" are meant to refer to complete protein regions from CD80 as well as partial regions which retain the activity of the complete region. For example, a functional V region of CD80 refers to amino acids 43-123 of CD80 or a fragment thereof, including proteins which include other sequences including but not limited to other CD80 sequences, which retains the ability to bind to CD28. A functional C region of CD80 refers to amino acids 155-223 of CD80 or a fragment thereof, including proteins which include other sequences including but not limited to other CD80 sequences, which retains the ability to bind to CDLA-4 and transmute a negative signal. Thus a protein free of a functional C region of CD80 may contain a fragment of amino acids 155-223 of CD80 but such a fragment does not bind to CDLA-4 and transmute a negative signal. Similar proteins free of a functional C region may include amino acids 155-223 if adjacent sequences are changed to render the C region non-functional through conformational or other changes. A functional tm of CD80 refers to amino acids 243-263 of CD80 or a fragment thereof which retains the anchor a mutant CD80 protein which comprises it into the cell membrane and thereby prevent secretion. A functional ct of CD80 refers to amino acids 264-288 of CD80 or any fragment thereof which is retained in the cytoplasm when the mutant CD80 protein is expressed.

As used herein, the terms "C region$^+$ CD80 proteins" and "C region proteins" are used interchangeably and are meant to refer to those proteins which comprise a functional CD80 C region and due to the presence of all or part of the C region, such molecules transmute the negative signal associated with wild type CD80 C region interactions with CTLA4.

One aspect of the present invention relates to improved methods and compositions for vaccination, particularly DNA vaccination in which DNA that encodes target immunogens is administered into the individual in whom the DNA is taken up and expressed and an immune response is generated against the immunogen. According to aspects of the invention, DNA that encodes a CD80ΔC mutant protein is co-delivered to the individual and the expression of such DNA produces the CD80ΔC mutant protein which enhances the immune response induced against the immunogen.

It has been discovered that the co-production of CD80ΔC mutant protein in cells of a vaccinated individual that are expressing target antigens results in an surprisingly enhanced immune response against the target antigen. By providing an expressible form of nucleotide sequence that encodes CD80ΔC mutant proteins, vaccines which function by expressing target antigen in the cells of the vaccinated individual, such as DNA vaccines, recombinant vector vaccines and attenuated vaccines, the vaccines are improved.

The co-production of CD80ΔC mutant proteins in cells producing antigens results in enhanced cellular immunity against the antigen. Accordingly, the present invention provides improved vaccines by providing a nucleotide sequence that encodes CD80ΔC mutant protein operably linked to necessary regulatory sequences for expression in vaccines as part of vaccines such as DNA vaccines, subunit avirulent recombinant vector vaccines and live attenuated vaccines. Alternatively, CD80ΔC mutant protein is delivered as a protein adjuvant together with an immunogen or gene construct encoding an immunogen.

According to some embodiments of the invention in which CD80ΔC mutants are provided as molecular adjuvants in immunization protocols, the CD80ΔC mutants contain either a functional CD80 V region or a functional CD86 V region. The CD80ΔC mutants do not contain a functional CD80 C region. In some embodiments, the C region is deleted and the V region is linked directly to the transmembrane region. In some embodiments the CD86 C region is inserted in place of the CD80 Cregion. In some embodiments, non-CD-80, non-CD86 sequences are included in the CD80ΔC mutants after the V region. Some embodiments include the CD80 transmembrane region. Some embodiments include the CD86 transmembrane region. In some embodiments, the CD80 transmembrane region is deleted and not substituted by any other sequences. Some embodiments include non-CD-80, non-CD86 sequences in place of the CD80 tm. Some embodiments include the CD80 cytoplasmic tail. Some embodiments include the CD86 cytoplasmic tail. In some embodiments, the CD80 cytoplasmic tail is deleted and not substituted by any other sequences. Some embodiments include non-CD-80, non-CD86 sequences in place of the CD80 ct. It has been discovered that in those embodiments in which the CD80ΔC mutants are delivered to the cells by the administration of genetic material which encodes the CD80ΔC mutant, those CD80ΔC mutants which include a transmembrane region and cytoplasmic tail are particularly effective in stimulating immune responses. In some embodiments, the CD80 tm and CD80 ct are provided. In some embodiments, the CD86 tm and CD86 ct are provided. In some embodiments, the CD80 tm and CD86 et are provided. In some embodiments, the CD86 tm and CD80 ct are provided. In those embodiments in which the CD80ΔC mutants are delivered to the cells by the administration of CD80ΔC mutant proteins, the CD80ΔC mutant proteins may be provided as a soluble protein in which the transmembrane region and cytoplasmic tail are deleted and, in some cases, replaced with a soluble moiety.

Aspects of the present invention relate to isolated proteins that comprises 80V, 80tm and 80ct and is free of 80C; wherein said protein comprises either 80V or 86V or both and optionally comprises one or more of 80tm, 86tm, 80ct and 86ct and wherein:

80V is the variable domain of CD80 or a functional fragment thereof;

86V is the variable domain of CD86 or a functional fragment thereof;

86C is the C domain of CD86 or a functional fragment thereof;

80 tm is the transmembrane region of CD80 or a functional fragment thereof;

86tm is the transmembrane region of CD86 or a functional fragment thereof;

80ct is the cytoplasmic tail of CD80 or a functional fragment thereof; and

86ct is the cytoplasmic tail of CD86 or a functional fragment thereof.

According to some embodiments, the have the formula:

$$R^1-R^2-R^3-R^4-R^5-R^6-R^7-R^8-R^9$$

wherein
$R^1$ is 0-50 amino acids;
$R^2$ is 80V or 86V;
$R^3$ is 0-50 amino acids;
$R^4$ is 86C or 0 amino acids;
$R^5$ is 0-50 amino acids;
$R^6$ is 80tm or 86tm;
$R^7$ is 0-50 amino acids;
$R^8$ is 80ct or 86ct; and
$R^9$ is 0-50 amino acids.

In some embodiments $R^1$ is 0-25 amino acids; $R^3$ is 0-25 amino acids; $R^5$ is 0-25 amino acids; $R^7$ is 0-25 amino acids; and/or $R^9$ is 0-25 amino acids.

In some embodiments $R^1$ is 0-10 amino acids; $R^3$ is 0-10 amino acids; $R^5$ is 0-10 amino acids; $R^7$ is 0-10 amino acids; and/or $R^9$ is 0-10 amino acids.

In some embodiments, the protein is a CD80 mutant selected from the group consisting of:
80V/dele/80tm/80ct;
80V/dele/80tm/86ct;
80V/dele/86tm/80ct;
86V/dele/80tm/80ct;
86V/dele/80tm/86ct;
86V/dele/86tm/80ct;
80V/dele/86tm/86ct;
80V/86C/80tm/80ct;
80V/86C/80 tm/86ct;
80V/86C/86tm/80ct;
86V/86C/80tm/80ct;
86V/86C/80tm/86ct;
86V/86C/86tm/80ct;
80V/86C/86tm/86ct;
80V/dele/80tm/dele;
80V/dele/86tm/dele;
86V/dele/80tm/dele;
80V/86C/80tm/dele;
80V/86C/86tm/dele;
86V/86C/80tm/dele;
86V/86C/80tm/dele;
86V/86C/dele/80ct;
80V/86C/dele/80ct;
80V/dele/dele/80ct;
86V/dele/dele/80ct;
80V/86C/dele/dele; and;
80V.

In some embodiments, the CD80 mutant has the formula selected from the group consisting of:
R-80V-R-dele-R-80tm-R-80ct-R;
R-80V-R-dele-R-80tm-R-86ct-R;
R-80V-R-dele-R-86tm-R-80ct-R;

R-86V-R-dele-R-80tm-R-80ct-R;
R-86V-R-dele-R-80tm-R-86ct-R;
R-86V-R-dele-R-86tm-R-80ct-R;
R-80V-R-dele-R-86tm-R-86ct-R;
R-80V-R-86C-R-80tm-R-80ct-R;
R-80V-R-86C-R-80tm-R-86ct-R;
R-80V-R-86C-R-86tm-R-80ct-R;
R-86V-R-86C-R-80tm-R-80ct-R;
R-86V-R-86C-R-80tm-R-86ct-R;
R-86V-R-86C-R-86tm-R-80ct-R;
R-80V-R-86C-R-86tm-R-86ct-R;
R-80V-R-dele-R-80tm-R-dele-R;
R-80V-R-dele-R-86tm-R-dele-R;
R-86V-R-dele-R-80tm-R-dele-R;
R-80V-R-86C-R-80tm-R-dele-R;
R-80V-R-86C-R-86tm-R-dele-R;
R-86V-R-86C-R-80tm-R-dele-R;
R-86V-R-86C-R-80tm-R-dele-R;
R-86V-R-86C-R-dele-R-80ct-R;
R-80V-R-86C-R-dele-R-80ct-R;
R-80V-R-dele-R-dele-R-80ct-R;
R-86V-R-dele-R-dele-R-80ct-R;
R-80V-R-86C-R-dele-R-dele-R; and
R-80V-R; wherein 80V is the variable domain of CD80 or a functional fragment thereof;

86V is the variable domain of CD86 or a functional fragment thereof;

86C is the C domain of CD86 or a functional fragment thereof;

80tm is the transmembrane region of CD80 or a functional fragment thereof;

86tm is the transmembrane region of CD86 or a functional fragment thereof;

80ct is the cytoplasmic tail of CD80 or a functional fragment thereof;

86ct is the cytoplasmic tail of CD86 or a functional fragment thereof;

dele is 0 amino acids; and

R are each independently 0-100 amino acids.

In some embodiments, R are each independently 0-50 amino acids.

In some embodiments, R are each independently 0-30 amino acids.

In some embodiments, R are each independently 0-20 amino acids.

In some embodiments of the invention, the CD80 mutant is selected from the group consisting of:

CD80 with the C domain deleted;

CD80 with the C domain deleted and a CD86 transmembrane region substituting the CD80 transmembrane region;

CD80 with the C domain deleted and a CD86 cytoplasmic tail region substituting the CD80 cytoplasmic tail region;

CD80 with the C domain deleted and a CD86 V domain substituting the CD80 V domain;

CD80 with the C domain deleted and a CD86 V domain substituting the CD80 V domain and a CD86 transmembrane region substituting the CD80 transmembrane region;

CD80 with the C domain deleted and a CD86 V domain substituting the CD80 V domain and a CD86 cytoplasmic tail region substituting the CD80 cytoplasmic tail region;

CD80 with the C domain deleted and a CD86 transmembrane region substituting the CD80 transmembrane region and a CD86 cytoplasmic tail region substituting the CD80 cytoplasmic tail region;

CD80 with a CD86 C domain substituting the CD80 C domain;

CD80 with a CD86 C domain substituting the CD80 C domain and a CD86 transmembrane region substituting the CD80 transmembrane region;

CD80 with a CD86 C domain substituting the CD80 C domain and a CD86 cytoplasmic tail region substituting the CD80 cytoplasmic tail region;

CD80 with a CD86 C domain substituting the CD80 C domain and a CD86 V domain substituting the CD80 V domain;

CD80 with a CD86 C domain substituting the CD80 C domain and a CD86 V domain substituting the CD80 V domain and a CD86 transmembrane region substituting the CD80 transmembrane region;

CD80 with a CD86 C domain substituting the CD80 C domain and a CD86 V domain substituting the CD80 V domain and a CD86 cytoplasmic tail region substituting the CD80 cytoplasmic tail region;

CD80 with a CD86 C domain substituting the CD80 C domain and a CD86 transmembrane region substituting the CD80 transmembrane region and a CD86 cytoplasmic tail region substituting the CD80 cytoplasmic tail region;

CD80 with the C domain deleted and the cytoplasmic tail region deleted;

CD80 with the C domain deleted and the cytoplasmic tail region deleted and a CD86 transmembrane region substituting the CD80 transmembrane region;

CD80 with the C domain deleted and the cytoplasmic tail region deleted and a CD86 V domain substituting the CD80 V domain;

CD80 with a CD86 C domain substituting the CD80 C domain and a CD86 transmembrane region substituting the CD80 transmembrane region and a CD86 cytoplasmic tail region substituting the CD80 cytoplasmic tail region;

CD80 with a CD86 C domain substituting the CD80 C domain and the cytoplasmic tail region deleted;

CD80 with a CD86 C domain substituting the CD80 C domain and the cytoplasmic tail region deleted and a CD86 transmembrane region substituting the CD80 transmembrane region;

CD80 with a CD86 V domain substituting the CD80 V domain and a CD86 C domain substituting the CD80 C domain and the cytoplasmic tail region deleted;

CD80 with a CD86 V domain substituting the CD80 V domain and a CD86 C domain substituting the CD80 C domain and the transmembrane region deleted;

CD80 with a CD86 C domain substituting the CD80 C domain and the transmembrane region deleted;

CD80 with the C domain deleted and the transmembrane region deleted;

CD80 with the C domain deleted and CD86 V domain substituting the CD80 V domain and the transmembrane region deleted;

CD80 with a CD86 C domain substituting the CD80 C domain and the transmembrane region deleted and the cytoplasmic tail region deleted;

CD80 with the domain deleted, the transmembrane region deleted and the cytoplasmic tail region deleted; and the CD80 variable domain or functional fragments thereof.

Protein forms of the CD80ΔC mutants can be formulated as components in vaccines or genetic constructs which include coding sequences that encode the CD80ΔC mutants may be provided as components of vaccines. In either case, such vaccines may be used in prophylactic or therapeutic methods.

According to some preferred embodiments of the invention, DNA vaccines are provided which contain DNA molecules that contain coding sequences encoding an immunogen and a CD80ΔC mutant. An improvement of the present invention relates to the inclusion of genetic material for the co-production of a CD80ΔC mutant protein in addition to the production of the antigenic target encoded by nucleic acid sequences of the DNA vaccines.

The present invention relates to methods of introducing genetic material into the cells of an individual in order to induce immune responses against proteins and peptides which are encoded by the genetic material. The methods comprise the steps of administering to the tissue of said individual, either a single nucleic acid molecule that comprises a nucleotide sequence that encodes a target protein and a nucleotide sequence that encodes a CD80ΔC mutant protein; or a composition having two nucleic acid molecules, one that comprises a nucleotide sequence that encodes a target protein and one that comprises a nucleotide sequence that encodes a CD80ΔC mutant protein. The nucleic acid molecule(s) may be provided as plasmid DNA, the nucleic acid molecules of recombinant vectors or as part of the genetic material provided in an attenuated vaccine.

According to the present invention, compositions and methods are provided which prophylactically and/or therapeutically immunize an individual against a pathogen or abnormal, disease-related cell. The genetic material that encodes a target protein, i.e. a peptide or protein that shares at least an epitope with an immunogenic protein found on the pathogen or cells to be targeted, and genetic material that encodes a CD80ΔC mutant protein. The genetic material is expressed by the individual's cells and serves as an immunogenic target against which an immune response is elicited. The resulting immune response reacts with a pathogen or cells to be targeted and is broad based: in addition to a humoral immune response, both arms of the cellular immune response are elicited. The methods of the present invention are useful for conferring prophylactic and therapeutic immunity. Thus, a method of immunizing includes both methods of protecting an individual from pathogen challenge, or occurrence or proliferation of specific cells as well as methods of treating an individual suffering from pathogen infection, hyperproliferative disease or autoimmune disease.

As used herein the terms "target protein" and "immunogen" are used interchangeably and are meant to refer to peptides and protein encoded by gene constructs which act as protein targets for an immune response. The target protein is a protein against which an immune response can be elicited. The target protein is an immunogenic protein which shares at least an epitope with a protein from the pathogen or undesirable cell-type, such as a cancer cell or a cell involved in autoimmune disease, against which immunization is required. The immune response directed against the target protein will protect the individual against and treat the individual for the specific infection or disease with which the target protein is associated. The target protein does not need to be identical to the protein against which an immune response is desired. Rather, the target protein must be capable of inducing an immune response that cross reacts to the protein against which the immune response is desired.

The present invention is useful to elicit broad immune responses against a target protein, i.e. proteins specifically associated with pathogens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

According to the present invention, DNA or RNA that encodes a target protein and a CD80ΔC mutant protein is introduced into the cells of tissue of an individual where it is expressed, thus producing the target protein and the CD80ΔC mutant protein. The DNA or RNA sequences encoding the target protein and the CD80ΔC mutant are each linked to regulatory elements necessary for expression in the cells of the individual. Regulatory elements for DNA expression include a promoter and a polyadenylation signal. In addition, other elements, such as a Kozak region, may also be included in the genetic construct. The preferred embodiments include nucleotide sequences encoding the target protein and CD80ΔC mutant protein provided as separate expressible forms in which each of the target protein and CD80ΔC mutant protein is linked to its own set of regulatory elements necessary for expression in the cell of the individual. However, the present invention additional relates to embodiments in which the target protein and CD80ΔC mutant protein are provided as a single genetic construct. In some such embodiment, the polyprotein which is produced by the single expressible form may be processed into two separate proteins or it may exist as a chimeric protein which functions both as the target protein and CD80ΔC mutant. In some embodiments, nucleic acid sequences encoding two or more copies of the target protein and/or two or more copies CD80ΔC mutant protein may be provided in a single expressible form of a gene construct. Polyproteins encoded therein may be processed into subunits following expression or maintained as functional polyproteins.

As used herein, the term "expressible form" refers to gene constructs which contain the necessary regulatory elements operable linked to a coding sequence that encodes a target protein and/or CD80ΔC mutant protein, such that when present in the cell of the individual, the coding sequence will be expressed.

As used herein, the term "sharing an epitope" refers to proteins which comprise at least one epitope that is identical to or substantially similar to an epitope of another protein.

As used herein, the term "substantially similar epitope" is meant to refer to an epitope that has a structure which is not identical to an epitope of a protein but nonetheless invokes an cellular or humoral immune response which cross reacts to that protein.

Genetic constructs comprise a nucleotide sequence that encodes a target protein and/or a CD80ΔC mutant protein operably linked to regulatory elements needed for gene expression. According to the invention, combinations of gene constructs which include one that comprises an expressible form of the nucleotide sequence that encodes a target protein and one that includes an expressible form of the nucleotide sequence that encodes a CD80ΔC mutant protein are provided. Incorporation into a living cell of the DNA or RNA molecule(s) which include the combination of gene constructs results in the expression of the DNA or RNA and production of the target protein and a CD80ΔC mutant protein. A surprisingly enhanced immune response against the target protein results.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, *listeria* and *shigella*. In addition, the present invention is also useful to immunize an individual against protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins. Table 1 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material which encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets.

Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HTLV or HBV.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. As used herein, the term "hyperproliferative-associated protein" is meant to refer to proteins that are associated with a hyperproliferative disease. To immunize against hyperproliferative diseases, a genetic construct that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins which are found at higher levels in tumor cells including the protein recognized by monoclonal antibody 17-IA and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include V$\beta$-3, V$\beta$-14, V$\beta$-17 and V$\alpha$-17. Thus, vaccination with a DNA construct that encodes at least one of these proteins will elicit an immune response that will target T cells involved in RA. See: Howell, M. D., et al., 1991 *Proc. Natl. Acad. Sci. USA* 88:10921-10925; Paliard, X., et al., 1991 *Science* 253:325-329; Williams, W. V., et al., 1992 *J. Clin. Invest.* 90:326-333; each of which is incorporated herein by reference.

In MS, several specific variable regions of TCRs which are involved in the disease have been characterized. These TCRs include Vβ-7 and Vα-10. Thus, vaccination with a DNA construct that encodes at least one of these proteins will elicit an immune response that will target T cells involved in MS. See: Wucherpfennig, K. W., et al., 1990 *Science* 248:1016-1019; Oksenberg, J. R., a al., 1990 *Nature* 345:344-346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

The present invention provides an improved method of immunizing individuals that comprises the step of delivering gene constructs to the cells of individuals as part of vaccine compositions which include are provided which include DNA vaccines, attenuated live vaccines and recombinant vaccines. The gene constructs comprise a nucleotide sequence that encodes an immunomodulating protein and that is operably linked to regulatory sequences that can function in the vaccine to effect expression. The improved vaccines result in an enhanced cellular immune response.

In some methods of immunizing, the individual is administered a gene construct encoding an immunogen and a genetic construct encoding a CD80ΔC mutant protein. In some methods of immunizing, the individual is administered a gene construct encoding both an immunogen and a CD80ΔC mutant protein. In some alternative methods of immunizing, the individual is administered an immunogen and a CD80ΔC mutant protein. In some alternative methods of immunizing, the individual is administered a protein immunogen and genetic construct encoding a CD80ΔC mutant protein. In some alternative methods of immunizing, the individual is administered a gene construct encoding an immunogen and a CD80ΔC mutant protein.

According to another aspect of the invention, CD80 C region proteins are provided to suppress immune responses associated with autoimmune diseases and transplant rejections. The CD80 C region proteins contain a functional CD80C region. Functional fragments of the CD80 C region can be identified routinely. In some embodiments, functional fragments of the CD80 C region are less than 60 amino acids. In some embodiments, functional fragments of the CD80 C region are less than 50 amino acids. In some embodiments, functional fragments of the CD80 C region are less than 40 amino acids. In some embodiments, functional fragments of the CD80 C region are less than 30 amino acids. In some embodiments, functional fragments of the CD80 C region are less than 20 amino acids. In some embodiments, functional fragments of the CD80 C region are less than 15 amino acids. In some embodiments, functional fragments of the CD80 C region are less than 10 amino acids.

In some embodiments, the V region is deleted. In some embodiments, the CD80 or CD86 V region is present. Some embodiments include the CD80 transmembrane region. Some embodiments include the CD86 transmembrane region. In some embodiments, the CD80 transmembrane region is deleted and not substituted by any other sequences. Some embodiments include non-CD-80, non-CD86 sequences. Some embodiments include non-CD-80, non-CD86 sequences in place of the CD80tm. Some embodiments include the CD80 cytoplasmic tail. Some embodiments include the CD86 cytoplasmic tail. In some embodiments, the CD80 cytoplasmic tail is deleted and not substituted by any other sequences. Some embodiments include non-CD-80, non-CD86 sequences in place of the CD80 ct.

According to some embodiments, the non-CD80 protein comprises at least the C domain of CD80 or a functional fragment thereof. As used herein, the term non-CD80 protein is meant to refer to a protein which differs from wildtype CD80 but comprises a CD80 C domain or a functional fragment thereof. In some embodiments, the non-CD80 protein have the formula:

$$R^1—R^2—R^3—R^4—R^5—R^6—R^7—R^8—R^9$$

wherein $R^1$ is 0-50 amino acids;

$R^2$ is 80V or 86V;

$R^3$ is 0-50 amino acids;

$R^4$ is 80C or 0 amino acids;

$R^5$ is 0-50 amino acids;

$R^6$ is 80tm or 86tm;

$R^7$ is 0-50 amino acids;

$R^8$ is 80ct or 86ct; and

R⁹ is 0-50 amino acids.
wherein
- 80V is the variable domain of CD80 or a functional fragment thereof;
- 86V is the variable domain of CD86 or a functional fragment thereof;
- 80C is the C domain of CD80 or a functional fragment thereof;
- 80tm is the transmembrane region of CD80 or a functional fragment thereof;
- 86tm is the transmembrane region of CD86 or a functional fragment thereof;
- 80ct is the cytoplasmic tail of CD80 or a functional fragment thereof; and
- 86ct is the cytoplasmic tail of CD86 or a functional fragment thereof.

According to some embodiments of the invention, the isolated non-CD80 protein that comprises at least the C domain of CD80 or a functional fragment thereof has the formula selected from the group consisting of:
R-dele-R-80C-R-80tm-R-80ct-R;
R-dele-R-80C-R-80tm-R-dele-R;
R-80V-R-80C-R-80tm-R-dele-R;
R-80V-R-80C-R-dele-R-dele-R;
R-86V-R-80C-R-80tm-R-80ct-R;
R-86V-R-80C-R-80tm-R-dele-R;
R-86V-R-80C-R-dele-R-dele-R;
R-80V-R-80C-R-86tm-R-80ct-R;
R-dele-R-80C-R-86tm-R-80ct-R;
R-dele-R-80C-R-86tm-R-dele-R;
R-80V-R-80C-R-86tm-R-dele-R;
R-80V-R-80C-R-80tm-R-86ct-R;
R-dele-R-80C-R-80tm-R-86ct-R;
R-86V-R-80C-R-86tm-R-80ct-R;
R-86V-R-80C-R-80tm-R-86ct-R;
R-86V-R-80C-R-86tm-R-dele-R;
R-dele-R-80C-R-86tm-R-86ct-R; and
R-86V-R-80C-R-86tm-R-86ct;
wherein
- 80V is the variable domain of CD80 or a functional fragment thereof;
- 86V is the variable domain of CD86 or a functional fragment thereof;
- 80C is the C domain of CD80 or a functional fragment thereof;
- 80tm is the transmembrane region of CD80 or a functional fragment thereof;
- 86tm is the transmembrane region of CD86 or a functional fragment thereof;
- 80ct is the cytoplasmic tail of CD80 or a functional fragment thereof;
- 86ct is the cytoplasmic tail of CD86 or a functional fragment thereof;
- dele is 0 amino acids; and
- each R is each independently 0-100 amino acids.

In some embodiments, each R is independently 0-50 amino acids; in some embodiments, each R is independently 0-30 amino acids; in some embodiments, each R is independently 0-20 amino acids.

In some embodiments of the invention, the non-CD80 protein is selected from the group consisting of:
- a mutant CD80 with the variable domain deleted;
- a mutant CD80 with the variable domain deleted and the cytoplasmic tail deleted;
- a mutant CD80 with the cytoplasmic tail deleted;
- a mutant CD80 with the transmembrane region deleted and the cytoplasmic tail deleted;
- a mutant CD80 with a CD86 variable domain substituted in place of the CD80 variable domain;
- a mutant CD80 with a CD86 variable domain substituted in place of the CD80 variable domain and the cytoplasmic tail deleted;
- a mutant CD80 with a CD86 variable domain substituted in place of the CD80 variable domain and the transmembrane region deleted and the cytoplasmic tail deleted;
- a mutant CD80 with a CD86 transmembrane region substituted in place of the CD80 transmembrane region;
- a mutant CD80 with the variable region deleted and a CD86 transmembrane region substituted in place of the CD80 transmembrane region;
- a mutant CD80 with the variable region deleted, the cytoplasmic tail deleted and a CD86 transmembrane region substituted in place of the CD80 transmembrane region;
- a mutant CD80 with the cytoplasmic tail deleted and a CD86 transmembrane region substituted in place of the CD80 transmembrane region;
- a mutant CD80 with a CD86 cytoplasmic tail substituted in place of the CD80 cytoplasmic tail;
- a mutant CD80 with the variable region deleted and a CD86 cytoplasmic tail substituted in place of the CD80 cytoplasmic tail;
- a mutant CD80 with a CD86 variable domain substituted in place of the CD80 variable domain and a CD86 transmembrane region substituted in place of the CD80 transmembrane region;
- a mutant CD80 with a CD86 variable domain substituted in place of the CD80 variable domain and a CD86 cytoplasmic tail substituted in place of the CD80 cytoplasmic tail;
- a mutant CD80 with a CD86 variable domain substituted in place of the CD80 variable domain and a CD86 transmembrane region substituted in place of the CD80 transmembrane region and the cytoplasmic tail deleted;
- a mutant CD80 with the variable domain deleted and a CD86 transmembrane region substituted in place of the CD80 transmembrane region and CD86 cytoplasmic tail substituted in place of the CD80 cytoplasmic tail; and
- a mutant CD80 with a CD86 variable domain substituted in place of the CD80 variable domain and a CD86 transmembrane region substituted in place of the CD80 transmembrane region and CD86 cytoplasmic tail substituted in place of the CD80 cytoplasmic tail.

The CD80 C region proteins are provided as either proteins or genetic constructs that encode CD80 C region. Delivery of genetic constructs which comprise coding sequences that encode the wild type CD80, dele/80C/80tm/80ct, dele/80C/80tm/86ct dele/80C/86tm/80ct or dele/80C/86tm/86ct provide particularly effective results in immunosuppression and treatment of autoimmune diseases.

The methods of this aspect of the invention are useful to treat autoimmune diseases and disorders. Those skilled in the art can identify individuals who have autoimmune diseases or disorders. Examples of autoimmune diseases and disorders include T cell mediated autoimmune diseases such as rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis, and B cell mediated autoimmune diseases such as Lupus (SLE), Grave's disease, myasthenia gravis, autoimmune hemolytic anemia, autoimmune thrombocytopenia, asthma, cryoglobulinemia, primary biliary sclerosis and pernicious anemia.

The methods of this aspect of the invention are also useful to suppress immune responses in individuals undergoing transplant procedures including cell transplants such as bone marrow and brain cell grafts, tissue transplants such as cornea and skin grafts and myoplasty procedures, and organ transplants such as liver, lung, kidney and heart.

The methods of making and delivering compositions of the present invention are generally the same for immunization protocols as well as non-immunogenic therapeutic protocols.

As used herein, the term "protein" is meant to include proteinaceous molecules including peptides, polypeptides and proteins. Some embodiments of the invention relate to delivery of proteins through the administration of nucleic acids, particularly DNA, and to methods of using the same. For example, in some methods of immunizing, nucleic acids that encode immunogenic proteins and CD80ΔC mutant proteins are administered to individuals. Likewise, in some methods of treating autoimmune diseases and preventing graft/transplant rejections by immunosuppression, nucleic acids that encode CD80 C region proteins are administered to individuals. As used herein, the term "gene constructs of the invention" is intended to mean gene constructs that include coding sequences which encode immunogenic proteins, CD80ΔC mutant proteins and CD80 C region proteins which each can be produced by similar means and which can be formulated and administered in a similar manner for use in methods of the invention.

DNA vaccines are described in U.S. Pat. No. 5,593,972, U.S. Pat. No. 5,589,466, PCT/US90/01515, PCT/US93/02338, PCT/US93/048131, and PCT/US94/00899, which are each incorporated herein by reference. In addition to the delivery protocols described in those applications, alternative methods of delivering DNA are described in U.S. Pat. Nos. 4,945,050 and 5,036,006, which are both incorporated herein by reference. DNA vaccine protocols are useful to immunize individuals. The teachings can be applied in the present invention to aspects in which individuals with autoimmune disease and transplant rejections are treated using gene constructs that encode CD80 C region proteins. In such embodiments, no coding sequences encoding immunogens are provided.

When taken up by a cell, the genetic constructs of the invention may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic constructs of the invention as a linear minichromosome including a centromere, telomeres and an origin of replication.

Genetic constructs of the invention include regulatory elements necessary for gene expression of a nucleic acid molecule. The elements include: a promoter, an initiation codon, a stop codon, and a polyadenylation signal. In addition, enhancers are often required for gene expression of the sequence that encodes the protein of the invention. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to human and bovine growth hormone polyadenylation signals, SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs of the invention can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode a target protein, a CD80ΔC mutant protein and, additionally, genes for proteins which further enhance the immune response against such target proteins. Examples of such genes are those which encode cytokines and lymphokines such as a-interferon, gamma-interferon, platelet derived growth factor (PDGF), GC-SF, GM-C SF, TNF, epidermal growth factor (EGF), IL-1, IL-2, IL-4, IL-6, IL-8, IL-10 and IL-12.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

The methods of the present invention, whether methods of immunizing or methods of immunosuppressing, comprise the step of administering nucleic acid molecules to tissue of the individual. In some preferred embodiments, the nucleic acid molecules are administered intramuscularly, intranasally, intraperatoneally, subcutaneously, intradermally, intravenously, by aerosol administration to lung tissue or topically or by lavage to mucosal tissue selected from the group consisting of vaginal, rectal, urethral, buccal and sublingual.

An aspect of the present invention relates to pharmaceutical compositions useful in the methods of the present invention. The pharmaceutical compositions comprise a nucleic acid molecule, preferably a DNA molecule comprising a nucleotide sequence that encodes one or more proteins operably linked to regulatory elements necessary for expression in the cells of the individual. The pharmaceutical compositions further comprise a pharmaceutically acceptable carrier or diluent. The term "pharmaceutical" is well known and widely understood by those skilled in the art. As used herein, the terms "pharmaceutical compositions" and "injectable pharmaceutical compositions" are meant to have their ordinary meaning as understood by those skilled in the art. Pharmaceutical compositions are required to meet specific standards regarding sterility, pyrogens, particulate matter as well as isotonicity and pH. For example, injectable pharmaceuticals are sterile and pyrogen free.

Pharmaceutical compositions according to the present invention may comprise about 1 ng to about 10,000 μg of DNA. In some preferred embodiments, the pharmaceutical compositions contain about 2000 μg, 3000 μg, 4000 μg or 5000 μg of DNA. In some preferred embodiments, the pharmaceutical compositions contain about 1000 μg of DNA. In some preferred embodiments, the pharmaceutical compositions contain about 10 ng to about 800 μg of DNA. In some preferred embodiments, the pharmaceutical compositions contain about 0.1 to about 500 μg of DNA. In some preferred embodiments, the pharmaceutical compositions-contain about 1 to about 350 μg of DNA. In some preferred embodiments, the pharmaceutical compositions contain about 25 to about 250 μg of DNA. In some preferred embodiments, the pharmaceutical compositions contain about 100 μg DNA.

The pharmaceutical compositions according to the present invention which comprise gene constructs of the invention are formulated according to the mode of administration to be used. One having ordinary skill in the art can readily formulate a vaccine or non-immunogenic therapeutic that comprises a genetic construct. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free. Pharmaceutical compositions according to the invention include delivery components in combination with nucleic acid molecules which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention. Suitable pharmaceutical carriers are described in Remington's Pharmaceutical Sciences, A. Osol, a standard reference text in this field, which is incorporated herein by reference.

In some embodiments, the nucleic acid molecule is delivered to the cells in conjunction with administration of a facilitating agent. Facilitating agents are also referred to as polynucleotide function enhancers or genetic vaccine facilitator agents. Facilitating agents are described in U.S. Pat. No. 5,830,876 issued Nov. 3, 1998, U.S. Pat. No. 5,593,972 issued Jan. 14, 1997 and International Application Serial Number PCT/US94/00899 filed Jan. 26, 1994 (U.S. Ser. No. 08/979,385 filed Nov. 29, 1997), which are each incorporated herein by reference. In addition, facilitating agents are described in U.S. Pat. No. 5,739,118 issued Apr. 14, 1998, U.S. Pat. No. 5,837,533 issued Nov. 17, 1998, PCT/US95/12502 filed Sep. 28, 1995 and PCT/US95/04071 filed Mar. 30, 1995, which are each incorporated herein by reference. Facilitating agents which are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with or without a facilitating agent include growth factors, cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10, IL-12 and B7.2 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalene, and hyaluronic acid. In embodiments which relate to methods of immunizing, co-agents are selected which preferably enhance immune responses. In embodiments which relate to methods of immunosuppressing, co-agents are selected which do not enhance immune responses.

In some preferred embodiments, the genetic constructs of the invention are formulated with or administered in conjunction with a facilitator selected from the group consisting of benzoic acid esters, anilides, amidines, urethan and the hydrochloride salts thereof such as those of the family of local anesthetics.

The facilitators in some preferred embodiments may be a compound having one of the following formulae:

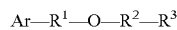
$$Ar-R^1-O-R^2-R^3$$
or

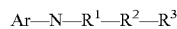
$$Ar-N-R^1-R^2-R^3$$
or

$$R^4-N-R^5-R^6$$
or

$$R^4-O-R^1-R^7$$

wherein:

Ar is benzene, p-aminobenzene, m-aminobenzene, o-aminobenzene, substituted benzene, substituted p-aminobenzene, substituted m-aminobenzene, substituted o-aminobenzene, wherein the amino group in the aminobenzene compounds can be amino, $C_1$-$C_5$ alkylamine, $C_1$-$C_5$, $C_1$-$C_5$ dialkylamine and substitutions in substituted compounds are halogen, $C_1$-$C_5$ alkyl and $C_1$-$C_5$ alkoxy;

$R^1$ is C=O;

$R^2$ is $C_1$-$C_{10}$ alkyl including branched alkyls;

$R^3$ is hydrogen, amine, $C_1$-$C_5$ alkylamine, $C_1$-$C_5$, $C_1$-$C_5$ dialkylamine;

$R^2$+$R^3$ can form a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle including a $C_1$-$C_{10}$ alkyl N-substituted heterocycle;

$R^4$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle;

$R^5$ is C=NH;

$R^6$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle; and.

$R^7$ is Ar, $R^2$ or $C_1$-$C_5$ alkoxy, a cyclic alkyl, a $C_1$-$C_{10}$ alkyl substituted cyclic alkyl, a cyclic aliphatic amine, a $C_1$-$C_{10}$ alkyl substituted cyclic aliphatic amine, a heterocycle, a $C_1$-$C_{10}$ alkyl substituted heterocycle and a $C_1$-$C_{10}$ alkoxy substituted heterocycle including a $C_1$-$C_{10}$ alkyl N-substituted heterocycle.

Examples of esters include: benzoic acid esters such as piperocaine, meprylcaine and isobucaine; para-aminobenzoic acid esters such as procaine, tetracaine, butethamine, propoxycaine and chloroprocaine; meta-aminobenzoic acid esters including metabuthamine and primacaine; and para-ethoxybenzoic acid esters such as parethoxycaine. Examples of anilides include lidocaine, etidocaine, mepivacaine, bupivacaine, pyrrocaine and prilocaine. Other examples of such compounds include dibucaine, benzocaine, dyclonine, pramoxine, proparacaine, butacaine, benoxinate, carbocaine, methyl bupivacaine, butasin picrate, phenacaine, diothan, luccaine, intracaine, nupercaine, metabutoxycaine, piridocaine, biphenamine and the botanically-derived bicyclics such as cocaine, cinnamoylcocaine, truxilline and cocaethylene and all such compounds complexed with hydrochloride.

In preferred embodiments, the facilitator is bupivacaine. The difference between bupivacaine and mepivacaine is that bupivacaine has a N-butyl group in place of an N-methyl group of mepivacaine. Compounds may have at that N, $C_1$-$C_{10}$. Compounds may be substituted by halogen such as procaine and chloroprocaine. The anilides are preferred.

The facilitating agent is administered prior to, simultaneously with or subsequent to the genetic construct. The facilitating agent and the genetic construct may be formulated in the same composition.

Bupivacaine-HCl is chemically designated as 2-piperidinecarboxamide, 1-butyl-N-(2,6-dimethylphenyl)-monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak (Rochester, N.Y.). Bupivacaine is commercially formulated with and without methylparaben and with or without epinephrine. Any such formulation may be used. It is commercially available for pharmaceutical use in concentration of 0.25%, 0.5% and 0.75% which may be used on the invention. Alternative concentrations, particularly those between 0.05%-1.0% which elicit desirable effects may be prepared if desired. According to the present invention, about 250 µg to about 10 mg of bupivacaine is administered. In some embodiments, about 250 µg to about 7.5 mg is administered. In some embodiments, about 0.05 mg to about 5.0 mg is administered. In some embodiments, about 0.5 mg to about 3.0 mg is administered. In some embodiments about 5 to 50 µg is administered. For example, in some embodiments about 50 µl to about 2 ml, preferably 50 µl to about 1500 µl and more preferably about 1 ml of 0.25-0.50% bupivacaine-HCl and 0.1% methylparaben in an isotonic pharmaceutical carrier is administered at the same site as the vaccine before, simultaneously with or after the vaccine is administered. Similarly, in some embodiments, about 50 µl to about 2 ml, preferably 50 µl to about 1500 µl and more preferably about 1 ml of 0.25-0.50% bupivacaine-HCl in an isotonic pharmaceutical carrier is administered at the same site as the vaccine before, simultaneously with or after the vaccine is administered. Bupivacaine and any other similarly acting compounds, particularly those of the related family of local anesthetics may be administered at concentrations which provide the desired facilitation of uptake of genetic constructs by cells.

In some embodiments of the invention, the individual is first subject to injection of the facilitator prior to administration of the genetic construct. That is, up to, for example, up to a about a week to ten days prior to administration of the genetic construct, the individual is first injected with the facilitator. In some embodiments, the individual is injected with facilitator about 1 to 5 days, in some embodiments 24 hours, before or after administration of the genetic construct. Alternatively, if used at all, the facilitator is administered simultaneously, minutes before or after administration of the genetic construct. Accordingly, the facilitator and the genetic construct may be combined to form a single pharmaceutical compositions.

In some embodiments, the genetic constructs are administered free of facilitating agents, that is in formulations free from facilitating agents using administration protocols in which the genetic constructions are not administered in conjunction with the administration of facilitating agents.

In some embodiments relating to immunization, gene constructs of the invention may remain part of the genetic material in attenuated live microorganisms or recombinant microbial vectors. In addition to using expressible forms of CD80 CD80ΔC mutant proteins coding sequences to improve genetic vaccines, the present invention relates to improved attenuated live vaccines and improved vaccines which use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the nucleotide sequence that encodes a CD80ΔC mutants protein is operably linked to regulatory sequences that can function in the vaccine to effect expression. The gene constructs are incorporated in the attenuated live vaccines and recombinant vaccines to produce improved vaccines according to the invention. Gene constructs may be part of genomes of recombinant viral vaccines where the genetic material either integrates into the chromosome of the cell or remains extrachromosomal. In some embodiments relating to non-immune response inducing therapy, nucleic acid molecules that encode CD80 C region protein may be delivered using any one of a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, transferrin-mediated transfection and other receptor-mediated means. The invention is intended to include such other forms of expression vectors and other suitable delivery means which serve equivalent functions and which become known in the art subsequently hereto. In a preferred embodiment of the present invention, DNA is delivered to competent host cells by means of an adenovirus. One skilled in the art would readily understand this technique of delivering DNA to a host cell by such means. Although the invention preferably includes adenovirus, the invention is intended to include any virus which serves equivalent functions. In another preferred embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

Some embodiments of the invention relate to proteins and methods of using the same. For example, in some methods of immunizing, immunogenic proteins and CD80ΔC mutant proteins are administered to individuals. Likewise, in some methods of treating autoimmune diseases and preventing graft/transplant rejections by immunosuppression, CD80 C region proteins are administered to individuals. As used herein, the term "proteins of the invention" is intended to mean immunogenic proteins, CD80ΔC mutant proteins and CD80 C region proteins which each can be produced by similar means and which can be formulated and administered in a similar manner for use in methods of the invention.

Vectors including recombinant expression vectors that comprises a nucleotide sequence that encodes proteins of the invention can be produced routinely. As used herein, the term "recombinant expression vector" is meant to refer to a plasmid, phage, viral particle or other vector which, when introduced into an appropriate host, contains the necessary genetic elements to direct expression of a coding sequence. One having ordinary skill in the art can isolate or synthesize a nucleic acid molecule that encodes a protein of the invention and insert it into an expression vector using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. Some embodiments of the invention relate to recombinant expression vectors comprises a nucleotide sequence that encodes a CD80ΔC mutant protein or a CD80 C region protein. The recombinant expression vectors of the invention are useful for transforming hosts. The present invention relates to a recombinant expression vectors that comprises a nucleotide sequence that encodes a CD80ΔC mutant protein, a chimeric protein which comprises a CD80ΔC mutant protein, or a CD80 C region protein.

The present invention relates to a host cell that comprises the recombinant expression vector that includes a nucleotide sequence that encodes a CD80ΔC mutant protein, a chimeric protein which comprises a CD806C mutant protein or a CD80C region protein. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of a CD80ΔC mutant protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce proteins of the invention using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

The expression vector including the DNA that encodes a protein of the invention is used to transform the compatible host which is then cultured and maintained under conditions wherein expression of the foreign DNA takes place. The protein of the invention thus produced is recovered from the culture, either by lysing the cells or from the culture medium as appropriate and known to those in the art. One having ordinary skill in the art can, using well known techniques, isolate the protein of the invention that is produced using such expression systems. The methods of purifying proteins of the invention from natural sources using antibodies which specifically bind to such protein are routine as is the methods of generating such antibodies (See: Harlow, E. and Lane, E., *Antibodies: A Laboratory Manual,* 1988, Cold Spring Harbor Laboratory Press which is incorporated herein by reference). Such antibodies may be used to purifying proteins produced by recombinant DNA methodology or natural sources.

Examples of genetic constructs include coding sequences which encode a protein of the invention and which are operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes proteins of the invention from readily available starting materials. Such gene constructs are useful for the production of proteins of the invention.

In addition to producing proteins of the invention by recombinant techniques, automated peptide synthesizers may also be employed to produce proteins of the invention. Such techniques are well known to those having ordinary skill in the art and are useful if derivatives which have substitutions not provided for in DNA-encoded protein production.

The proteins of the invention may be prepared by any of the following known techniques. Conveniently, the proteins of the invention may be prepared using the solid-phase synthetic technique initially described by Merrifield, in *J. Am. Chem. Soc.,* 15.2149-2154 (1963) which is incorporated herein by reference. Other protein synthesis techniques may be found, for example, in M. Bodanszky et al., (1976) *Peptide Synthe-* sis, John Wiley & Sons, 2d Ed. which is incorporated herein by reference; Kent and Clark-Lewis in *Synthetic Peptides in Biology and Medicine*, p. 295-358, eds. Alitalo, K., et al. Science. Publishers, (Amsterdam, 1985) which is incorporated herein by reference; as well as other reference works known to those skilled in the art. A summary of synthesis techniques may be found in J. Stuart and J. D. Young, *Solid Phase Peptide Synthelia*, Pierce Chemical Company, Rockford, Ill. (1984) which is incorporated herein by reference. Synthesis by solution methods may also be used, as described in *The Proteins*, Vol. II, 3d Ed., p. 105-237, Neurath, H. et al., Eds., Academic Press, New York, N.Y. (1976) which is incorporated herein by reference. Appropriate protective groups for use in such syntheses will be found in the above texts, as well as in J. F. W. McOmie, *Protective Groups in Organic Chemistry*, Plenum Press, New York, N.Y. (1973) which is incorporated herein by reference.

In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

In some embodiments, proteins may be produced in transgenic animals. The present invention relates to a transgenic non-human mammal that comprises the recombinant expression vector that comprises a nucleic acid sequence that encodes a CD80ΔC mutant protein or CD80 C region protein. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes the CD80ΔC mutant protein or CD80 C region protein is operably linked to a mammary cell specific promoter whereby the coding sequence is only expressed in mammary cells and the recombinant protein so expressed is recovered from the animal's milk. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce a CD80ΔC mutant protein or CD80C region protein. Preferred animals are goats, and rodents, particularly rats and mice.

Conservative substitutions of amino acid sequences of proteins of the invention are contemplated. As used herein, the term "conservative substitutions" is meant to refer to amino acid substitutions of CD80 residues with other residues which share similar structural and/or charge features. Those having ordinary skill in the art can readily design proteins of the invention with conservative substitutions for amino acids based upon well known conservative groups.

The pharmaceutical compositions of the present invention may be administered by any means that enables the active agent to reach the agent's site of action in the body of a mammal. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Because peptides are subject to being digested when administered orally, oral formulations are formulated to enterically coat the active agent or otherwise protect it from degradation in the stomach (such as preneutralization). Parenteral administration includes intravenous drip, subcutaneous, intraperitoneal or intramuscular injection, pulmonary administration, e.g., by inhalation or insufflation, or intrathecal or intraventricular administration. In preferred embodiments, parenteral administration, i.e., intravenous, subcutaneous, transdermal, intramuscular, is ordinarily used to optimize absorption. Intravenous administration may be accomplished with the aid of an infusion pump. The pharmaceutical compositions of the present invention may be formulated as an emulsion.

One skilled in the art would readily comprehend the multitude of pharmaceutically acceptable media that may be used in the present invention. Suitable pharmaceutical carriers are described in *Remington's Pharmaceutical Sciences*, A. Osol, a standard reference text in this field, which is incorporated herein by reference. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intravenous, intrathecal or intraventricular administration may include sterile aqueous solutions which may also contain buffers, diluents and other suitable additives and are preferably sterile and pyrogen free. Pharmaceutical compositions which are suitable for intravenous administration according to the invention are sterile and pyrogen free. For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Formulation of therapeutic compositions and their subsequent administration is believed to be within the skill of those in the art. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

Depending upon the method for which the protein or proteins are being administered, the pharmaceutical compositions of the present invention may be formulated and administered to most effectively. Modes of administration will be apparent to one skilled in the art in view of the present disclosure.

The methods of the present invention are useful in the fields of both human and veterinary medicine. Accordingly, the present invention relates to genetic immunization of mammals, birds and fish. The methods of the present invention can be particularly useful for mammalian species including human, bovine, ovine, porcine, equine, canine and feline species.

The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLE

In an effort to determine why CD86, but not CD80, is required for augmentation of T-cell responses, and to further study the structure function analysis of CD80 and CD86 which has revealed several critical areas involved in binding to CD28 and CTLA-4 including residues found on both the V- and C-domains of CD80, the role of different regions of CD80 and CD86 molecules in T-cell activation were examined using coimmunization of mice with DNA immunogen and DNA encoding chimeric or truncated forms of CD80 and CD86 molecules.

METHODS

Preparation of Constructs:

A DNA vaccine construct encoding for the HIV-1$_{MN}$ envelope protein (pcEnv) was prepared as described in U.S. Pat. No. 5,593,972. Human CD80 and CD86 genes were cloned from B cell cDNA library (Clontech, Palo Alto, Calif.) and placed into pSRαneo1+, an expression vector. More specifically, both CD80 and CD86 genes were PCR amplified as described in Kim, et al. (1997) Nature Biot. 15:641-645, which is incorporated herein by reference, and ligated into pSRαneo1+ downstream of the SRα promoter to make pCD80 and pCD86 expression vectors. The chimeric and truncated variants of these two genes were generated by PCR amplification using the Expand™ High Fidelity Polymerase system (Boehringer-Mannheim, Germany). For construction of all these forms of costimulatory molecules, pCD80 or pCD86 were used as the PCR templates. The following primers have been used in these reactions:

```
                                        SEQ ID NO: 1
A: CTGCTTGCTCAACTCTACGTC - (forward, vector)

SEQ ID NO: 2
B: CTGAAGTTAGCTTTGACTGATAACG - (reverse, CD80)

SEQ ID NO: 3
C: GCAATAGCATCACAAATTTCA - (reverse, vector)

SEQ ID NO: 4
D: CAGTCAAAGCTAACTTCAGTCAACC - (forward, CD86)

SEQ ID NO: 5
E: GGGAAGTCAGCAAGCACTGACAGTTC - (reverse, CD86)

SEQ ID NO: 6
F: TCAGTGCTTGCTGACTTCCCTACACC - (forward, CD80)

SEQ ID NO: 7
G: TCTTGCTTGGCTTTGACTGATAACGTCAC - (reverse, CD80)

SEQ ID NO: 8
H: TCAGTCAAAGCCAAGCAAGAGCATTTTCC - (forward, CD80)

SEQ ID NO: 9
I: TCCTCAAGCTCAAGCACTGACAGTTC - (reverse, CD86)

SEQ ID NO: 10
J: TCAGTGCTTGAGCTTGAGGACCC - (forward, CD86)

SEQ ID NO: 11
K: TCTGGATCCTCATCTTGGGGCA - (reverse, CD80)

SEQ ID NO: 12
L: TCTGGATCCTCATTTCCATAG - (reverse, CD86)
```

The V-domain of CD80 was amplified using A and B primers, the C-domain, transmembrane (TM) and cytoplasmic tail (T) of CD86 were amplified using C and D primers. These fragments were then purified, combined and used as templates in second step PCR reaction using forward (CTGCTTGCTCAACTCTACGTC-SEQ ID NO:1) and reverse (GCAATAGCATCACAAATTTCA-SEQ ID NO:3) primers. The PCR product was ligated into the pSRαneo1+ vector and the resultant plasmid (pV80C86T86) encodes a chimeric costimulatory molecule expressing the V-domain of CD80 and C-, TM-, and T-regions of CD86. The chimeric crossover point is at the conserved alanine 106 in CD80 and alanine 111 in CD86 position and respects the exon boundary.

The next plasmid pV86C80T80 which encoded CD86 V-domain and CD80 C-, TM-, and T-regions was constructed by amplification of CD86 V-region, using A and E primers. The PCR fragment encoding C, TM-, and T-domains of CD80 was amplified using C and F primers. The second stage PCR and cloning was performed as mentioned above.

Truncated forms of costimulatory molecules without C-domain (pV80CΔT80, pV86CΔT86) were also prepared by two step PCR technique. In case of pV80CΔT80 the V-domain was amplified using the A and G primers, whereas in case of pV86C(T86 V-domain was amplified using A and I primers. The TM/T fragments of both C-domain truncated molecules were amplified using C/H primers in case of pV80C(T80 and C/J in case of pV86CDT86. The resultant constructs were prepared by amplification and cloning the PCR products into the pSRaneo1+ expression vector. All constructs were verified by sequence to be faithful to the original wildtype CD80 and CD86 templates. The resulting deletion mutants lacked amino acid aspartate 107 through threonine 200 in CD80 and alanine 111 through isoleucine 211 in CD86. Of note both molecules were constructed to retain 6 to 7 membrane proximal amino acids of the respective C-domain.

Finally, the T-region deletion of pCD80 (pV80C80T( ) and pCD86 (pV86C86TΔ) were generated by a single step PCR using in both cases A as forward and K and L as reverse primers, respectively. The PCR products were cloned into the pSR(neo1+ vector. The encoded CD80 protein terminates after the first cytoplasmic tail amino acid residue, arginine. The resulting gene for CD86 molecule terminated after nucleotide 942 preserving the first lysine in the cytoplasmic tail.

All chimeric and truncated constructs as well as the wildtype molecules were cloned into the SRαneo1+ vector. Gene expression is under the control of the SRα promoter which is composed of the simian virus 40 (SV40) early promoter and the R-segment and part of the U5 sequence (R-U5') of the long terminal repeat of human T-cell leukemia virus type 1. All constructs were verified by sequencing to be faithful to the original wildtype CD80 and CD86 templates.
Expression of Plasmids:

Expression of these constructs were analyzed by immunofluorescence and flow cytometry (FACS) assays, using human rhabdomyosarcoma (RD) cells transfected with experimental or control plasmids. Cells were transfected by electroporation using 500 μF capacitance and 0.25 voltage using Gene Pulse (Bio-Rad, Hercules, Calif.).

For immunofluorescence assay transfected cells were incubated for 2 days and than transferred into Falcon® culture slides (Becton Dickinson, Bedford, Mass.). The following day the cells were washed, fixed with methanol (30', RT), and incubated with anti-CD80 (Coulter, Miami, Fla.) or CD86 (Pharmingen, San Diego, Calif.) monoclonal antibodies (1.5 hrs, 37° C.). The slides were washed and stained with goat-anti mouse IgG (Boehringer Mannheim, Indianapolis, Ind.) during 1.5 hrs at 37° C. The slides were viewed with a Nikon OPTIPHOT fluorescence microscope (Nikon Inc., Tokyo, JAPAN) and photographs were obtained.

For FACS analysis RD cells were transfected with mixture of constructs encoding CD80 or CD86 molecules (2 μg) and green fluorescent protein expression vector {10 μg (pcGFP from Clontech, Palo Alto, Calif.)}. The latter was used as a control plasmid for calculation of the efficacy of transfection. The expression of experimental plasmids was confirmed using monoclonal antibodies to the V-domain of CD80 or CD86 molecules (both from Pharmingen, San Diego, Calif.) conjugated with PE. Briefly, 1 μg of either anti-B7 antibodies were added to transfected or control cells ($10 \times 10^5$). Data were analyzed by FACScan with CELLQuest™ data acquisition and software (Becton Dickinson Immunocytometry Systems, San Jose, Calif.). The efficacy of transfection (fluorescence intensity) of cells expressing different B7 molecules was measured in the population of cells expressing GFP.
Immunization of Animals:

Each Balb/c mouse received three intramuscular injections (two weeks apart) with 50 μg of each DNA construct resuspended in 100 μl of phosphate buffered saline (PBS) and 0.25% bupivacaine-HCl (Sigma, St. Louis, Mo.). This dose was selected to maximize the enhancement of anti-viral immune responses provided by the simultaneous delivery of different molecular adjuvants (i.e. mutated, truncated, or wildtype costimulatory genes). 50 μg of plasmid, encoding HIV-1 gp160 envelope (pcEnv) was injected alone or as a mixture of pcEnv and 50 μg of the various CD80/86 constructs (molecular adjuvants). As a control naive mice and animals injected with control vectors were used. In several experiments animals were injected three times with the mixture of two molecular adjuvants (100 μg total) plus pcEnv (50 μg). Two weeks after the last injection, splenocytes from all experimental and control animals were isolated and used for detection of T-cell responses and cytokine production.
Immunohistochemical Assays on Muscle Cells:

Immunized leg muscle was examined immunohistochemically for detection of infiltration (presence of lymphocytes in muscle). Briefly, mouse quadriceps muscle was inoculated with 50 μg of pcEnv mixed with 50 μg of experimental or control plasmids. Seven days following inoculation, the mice were sacrificed and the quadriceps muscles were removed. The fresh muscle tissue was then frozen in O.C.T. compound (Sakura Finetek USA, Inc., Torrance, Calif.) and four micron frozen sections were made. The degree of inflammation was determined by examining hematoxylin and eosin (H&E) stained muscle sections.
Cytotoxic T Lymphocyte Assay:

A five hour $^{51}$Cr release CTL assay was performed. Briefly, the effectors were stimulated six days in the presence of stimulator cells and 10% RAT-T-STIM without Con A (Becton Dickinson Labware, Bedford, Mass.). For antigenic stimulation, 0.1% glutaraldehyde fixed P-815 cells infected with recombinant vaccinia virus which express HIV-1 envelope protein (vMN462) (NIH AIDS Research and Reference Reagent Program) were used. As target cells, P-815 cells infected with the recombinant (vMN462, specific) or with wildtype (WR, non-specific) vaccinia virus were used. Both target cells were labeled with 100 (Ci/ml $Na_2^{51}CrO_4$ and mixed with effector cells at effector: target (E:T) ratios ranging from 100:1 to 12.5:1. The percent specific lysis was determined as described in Kim, 1997 supra. Maximum and minimum release was determined by lysis of target cells in 10% Triton X-100 and medium, respectively. An assay was not considered valid if the value for the 'spontaneous release' counts were in excess of 20% of the 'maximum release'. To calculate specific lysis of targets, the percent lysis of non-specific targets was subtracted from the percent lysis of specific targets. In some experiments CD8+ T-cells were removed from culture of splenocytes by treatment with anti-CD8 monoclonal antibodies (53-6.7, ATCC) followed by incubation with non-toxic rabbit complement (Sigma).
Cytokine Production:

The level of various cytokines released by immune cells reflects the direction and magnitude of the immune response. Therefore, supernatant from the effector cells stimulated in vitro for CTL assay was collected and tested them for the release of γIFN, IL-4, and IL-12 using available ELISA kits (Biosource, Camarillo, Calif.).

RESULTS

Expression of Plasmids, Encoding Wildtypes and Mutated Forms of CD80 and CD86:

The expression of different forms of CD80 or CD86 constructs into the RD muscle tumor cells transiently transfected with control or experimental plasmids was analyzed first. Using an immunofluorescence technique, is was observed that experimental, but not control cells (transfected with vector alone) produced wildtype as well as all the different forms of mutated costimulatory molecules. The transfection efficiencies of these molecules were studied by FACS analysis. In these experiments a mixture of control plasmid, encoding GFP and experimental constructs, encoding different forms of costimulatory molecules, were transfected. The fluorescence intensity of cells expressing B7 molecules was detected only in the population of cells expressing GFP. The results demonstrated that majority of chimeric and truncated forms of CD86 and CD80 and CD86 wildtype molecules have been expressed similarly (Table 3). Only two constructs, encoding CD80 wildtype (pCD80) and cytoplasmic tail deleted CD86 (pV86C86TΔ) were expressed on the surface of transfected cells relatively higher than other plasmids.

Both CD86 and CD80 V-Domains are Important for the Activation of Virus-Specific CTL Response and Th1 Cytokine Production The B7 molecules play a critical role in inducing antigen-specific T-cell activation via triggering of appropriate ligands expressed on these cells. Earlier, it was reported that co-administration of wildtype CD86, but not CD80 cDNA along with DNA immunogen enhanced antigen-specific T-cell responses (Kim et al. 1997 Supra). To determine the role of the V-region of CD86 in this activation, these domains of CD80 and CD86 were exchanged (Table 3) and communized mice with constructs encoding these molecules along with plasmid encoding viral proteins. As a positive control, constructs expressing wildtype CD80 and CD86 were coinjected along with DNA immunogen, negative control mice received only the vector. Two weeks after the last immunization anti-virus CTL responses were analyzed in the cultures of splenocytes.

A background level of specific killing was observed in splenocytes obtained from the control animals and a low level killing was observed in animals coimmunized with pcEnv or pcEnv plus pCD80. However, mice coimmunized with pcEnv and pCD86 resulted in a high level of envelope-specific CTL (Table 4). Therefore, using the CD80 and CD86 genes inserted in the pSRaneo1+ vector, instead of the previously used pCDNA3 vector, CD80 and CD86 were confirmed to play differential roles in the modulation of cellular immune responses following DNA vaccination. Anti-viral CTL responses were next analyzed in mice immunized with chimeric molecules. Coimmunization of mice with pV86C80T80 and pcEnv did not generate virus-specific cytotoxic cells, but immunization of mice with mixture of pV80C86T86 and pcEnv induced more than 40% anti-HIV-1 CTL activity at E:T ratio 1:100. This response was similar to anti-viral CTL activity in mice coinjected with pcEnv plus pCD86 (Table 4). Thus, V region of CD80 was as important for antigen-specific T-cell activation as the V-region of the CD86 molecule, if it was expressed with the C-domain and cytoplasmic tail of the CD86 molecule. However, the V-domain of CD86 was functionally silent when expressed with C-domain and cytoplasmic tail of CD80. These results were supported by cytokine production data. Supernatant from splenocytes obtained from mice injected with pcEnv and pcEnv plus pCD80 induced low level of IL12, but not γIFN or IL4 production (Table 4). In contrast, coimmunization with pcEnv+pCD86 and pcEnv+pV80C86T86 induced significant antigen-specific enhancement of both γIFN and IL12 (Table 4), but not IL4 production.

These results would suggest that the C-domain and/or cytoplasmic tail of CD86 are important in positive signaling to T-cells, whereas the same domains of CD80 are not. Alternatively, the C-domain and/or cytoplasmic tail of CD80 might be involved in providing of negative signals to T-cells.

Cytoplasmic Tail of CD86 Crucial for Antigen-Specific T-Cell Activation

It has been demonstrated that the cytoplasmic tail of B7 is required for in vitro T-cell costimulation by allowing for ligand clustering on the cell surface. Thus, to demonstrate the role of the cytoplasmic tails of the B7 in 1-cell costimulation, cytoplasmic tail deleted mutants of B7 were constructed and coinjected mice with these plasmids (pV80C80TΔ or pV86C86TΔ) and pcEnv. Both constructs, encode truncated forms of CD80 or CD86 molecules induced lower level killing, whereas animals coimmunized with a mixture of pcEnv and pCD86 demonstrated strong anti-viral CTL responses (Table 4). Supportive data was generated by analyzing Th1 cytokine production.

Both CD80 and CD86 constructs without cytoplasmic tails did not enhance γIFN production after coinjection with DNA vaccine. Communization of mice with pV86C86TΔ induced a small increase of IL12 production compared with mice injected with pcEnv or pcEnv plus pV80C80TΔ: Importantly, control animals coimmunized with pcEnv plus DNA encoding wildtype of CD86 induce significant enhancement of both γIFN and IL12 cytokine production (Table 4). Thus, the cytoplasmic tail of CD86 molecule was important for T-cell activation. However, mice coimmunized with pcEnv plus pV80C80TΔ did not induce T-cell activation. Therefore, the involvement of the C-domain and/or cytoplasmic tail of CD80 in negative signaling remained undetermined. To resolve this question next C-domain deletion mutants of CD80 and CD86 were constructed.

C-Domain, but not Cytoplasmic Tail of CD80, is Involved in Providing of a Negative Signal to T-Cells.

Figure 2A:
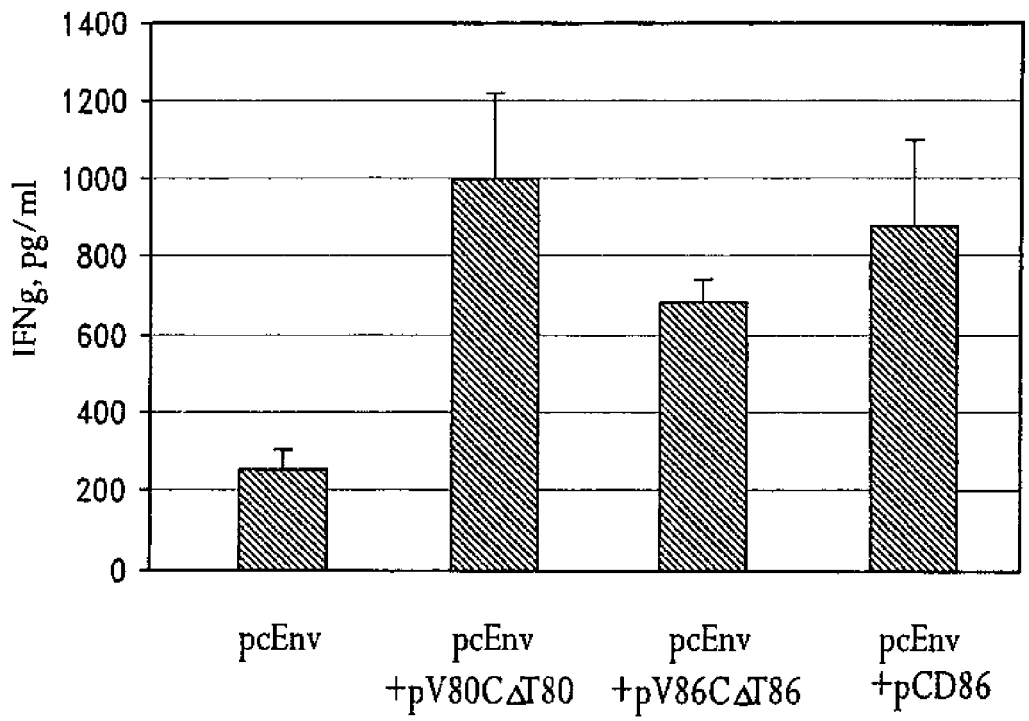
FIGS. 2A and 2B show data from experiments described in the Example showing lymphokine production induced by various constructs.
Figure 2B:
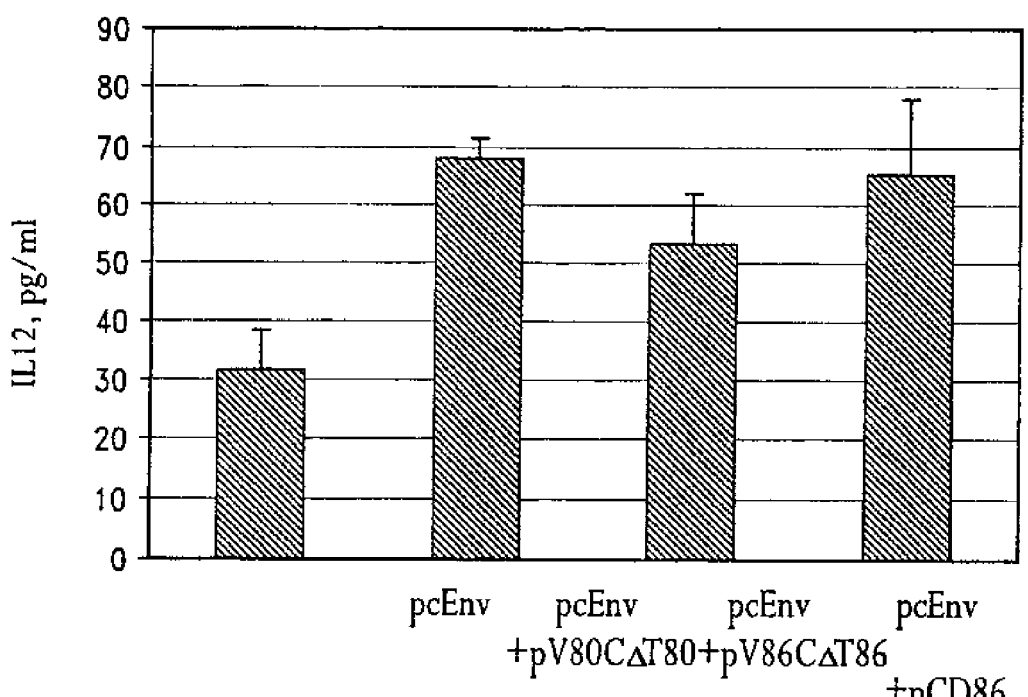

In the next set of experiments mice were coimmunized with pcEnv immunogen and plasmids, encoding only the V-domain and cytoplasmic tail of either CD80 (pV80CΔT80) or CD86 (pV86CΔT86) molecules. As controls, mice injected with only pcEnv or with pcEnv plus either pCD80 or pCD86. The antigen specific anti-viral CTL responses from these experiments are presented in FIG. 1. The adjuvant effect of CD86 was dramatic and was retained in lesser extend in the CD86 C-domain deletion molecule. In sharp contrast to the very poor effect in T-cell activation induced by wildtype and cytoplasmic tail deleted forms of CD80 (FIG. 1, Table 4), pV80CΔT80 was very effective at costimulating the anti-Env CTL response (FIG. 1), demonstrating gain of function through the loss of C-domain. To further investigate the enhancement of cellular immunity, production of Th1 cytokines was investigate using splenocytes of mice immunized with pcEnv and plasmids, encoding C-domain deleted CD80 or CD86 molecules. As controls, mice coimmunized with pcEnv plus either pCD80 or pCD86. Both pV86CΔT86 and pV80CΔT80 chimeric genes as well as DNA encoded wildtype CD86 coinjected along with pcEnv induced Th1 lymphokine production equally well (FIGS. 2A and 2B).

These results demonstrate that the cytoplasmic tail of CD80 is functional and is important for T-cell activation in vivo. More importantly, the data support the conclusion that the C-domain of CD80, but not CD86, can provide a "negative" signal to T-cells. Next, the inhibitory role of the CD80 C-domain in T-cell activation was analyzed.

C-Domain of CD80 Inhibits T-Cell Activation by CD86 Molecules.

To demonstrate the involvement of the C-domain of CD80 in providing a negative signal to antigen-specific T-cells, animals were immunized with the DNA immunogen and a combination of molecular adjuvants. Experimental mice were coimmunized with DNA immunogen and mixture of pCD86 with pCD80 or pCD86 with pV80CDT80. Control animals were injected with only pcEnv or coinjected with pcEnv plus pCD86, pCD80 or pV80C(T80. Anti-viral CTL assays were performed with splenocytes obtained from experimental and control mice.

Figure 3:
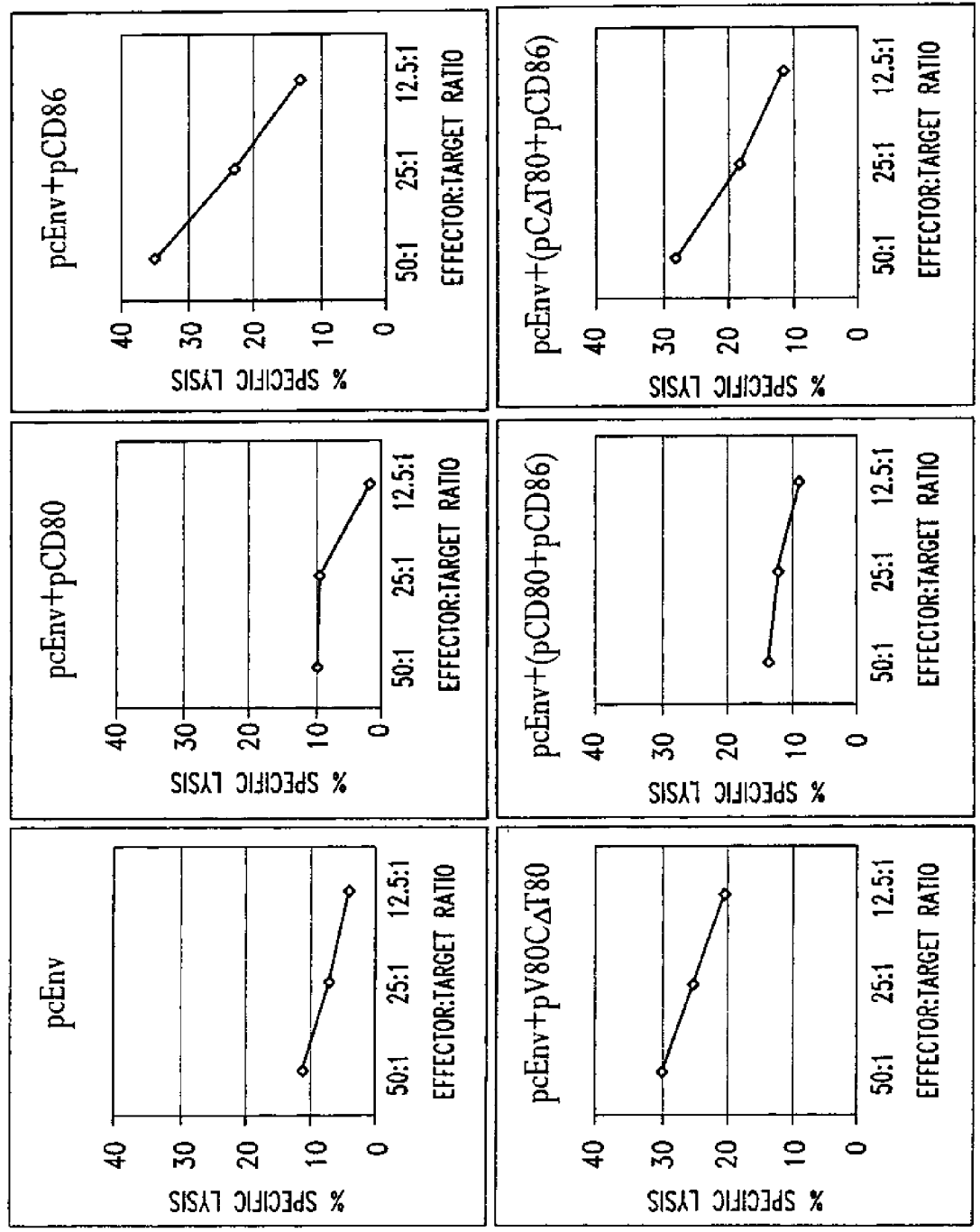
FIG. 3 shows data from experiments described in the Example showing CTL activity following administration of constructs.
Figure 4:
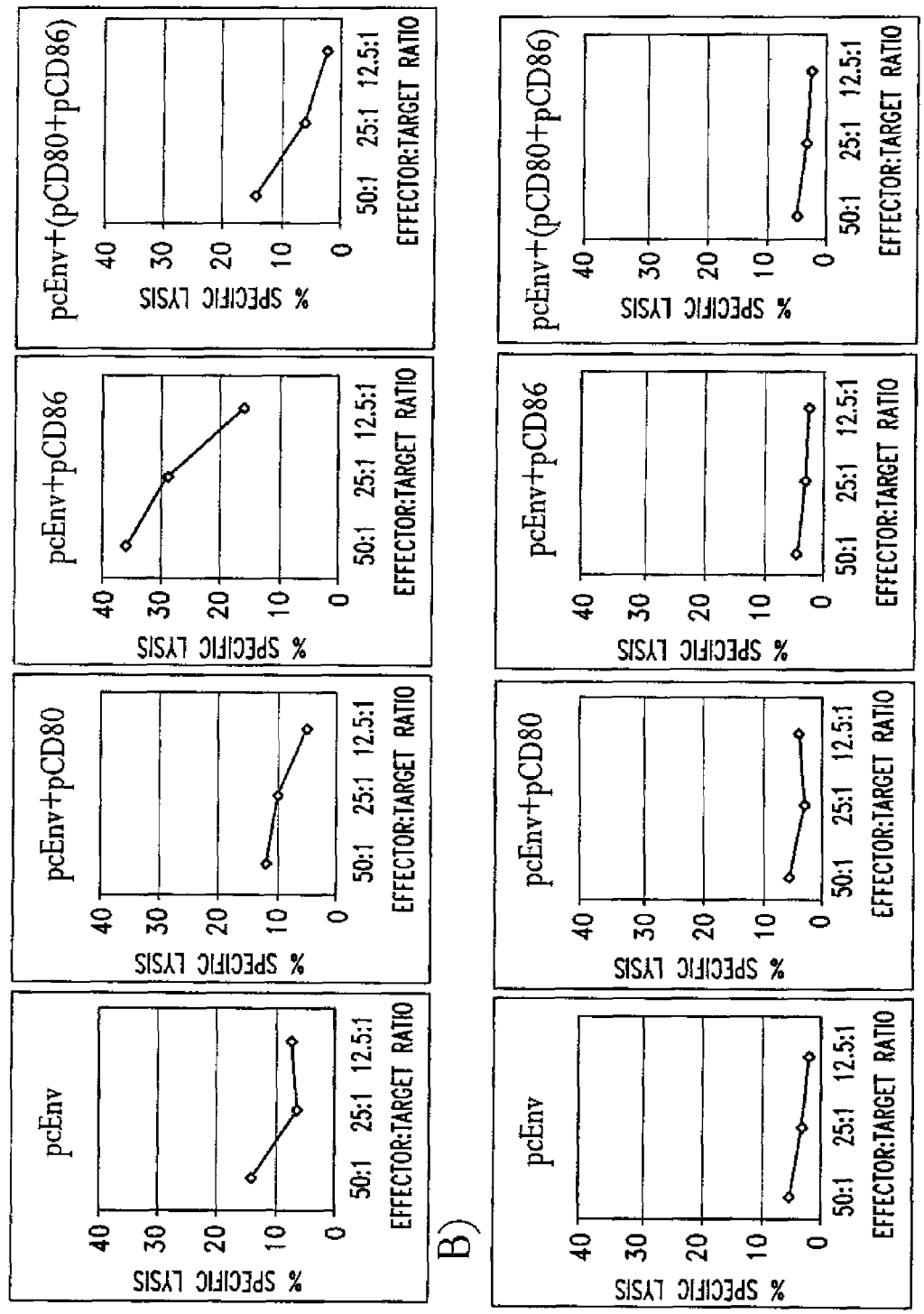
FIG. 4 shows data from experiments described in the Example showing CTL activity following administration of constructs measured after the removal of this population of cells.

As observed before coimmunization of mice with DNA immunogen and pCD86 or pV80C(T80 induced significant enhancement of CTL activity (FIG. 3). However, mice coimmunized with pcEnv and combination of wildtypes molecular adjuvants (pCD86+pCD80) did not enhance the CTL response (lysis was not more than in control group with pcEnv). Importantly, the combination of pCD86 and pV80CDT80 still induced an adjuvant effect in vaccinated animals and this effect was similar to effect induced in animals immunized with pCD86 plus DNA immunogen. Therefore, wildtype CD80, but not C-domain deleted mutant CD80 inhibited enhancement of anti-viral CTL responses when codelivered with the DNA immunogen. To verify the role of CD8+ T cells in the cytotoxic activity observed, CTL activity was measured after the removal of this population of cells. The splenocytes were treated with anti-CD8 monoclonal antibodies and non-toxic rabbit complement. The removal of $CD8^+$ T-cells resulted in the suppression of the anti-viral CTL activity in mice coinjected with DNA immunogen and pCD86. Again no anti-HIV-1 CTL activity was observed in mice coimmunized with pcEnv+pCD80+pCD86 (FIG. 4). Expression of C-Domain Deleted CD80 Induced Greater Infiltration of Lymphocytes into the Muscle of Immunized Animals than Expression of Wildtype CD80.

Figure 5:
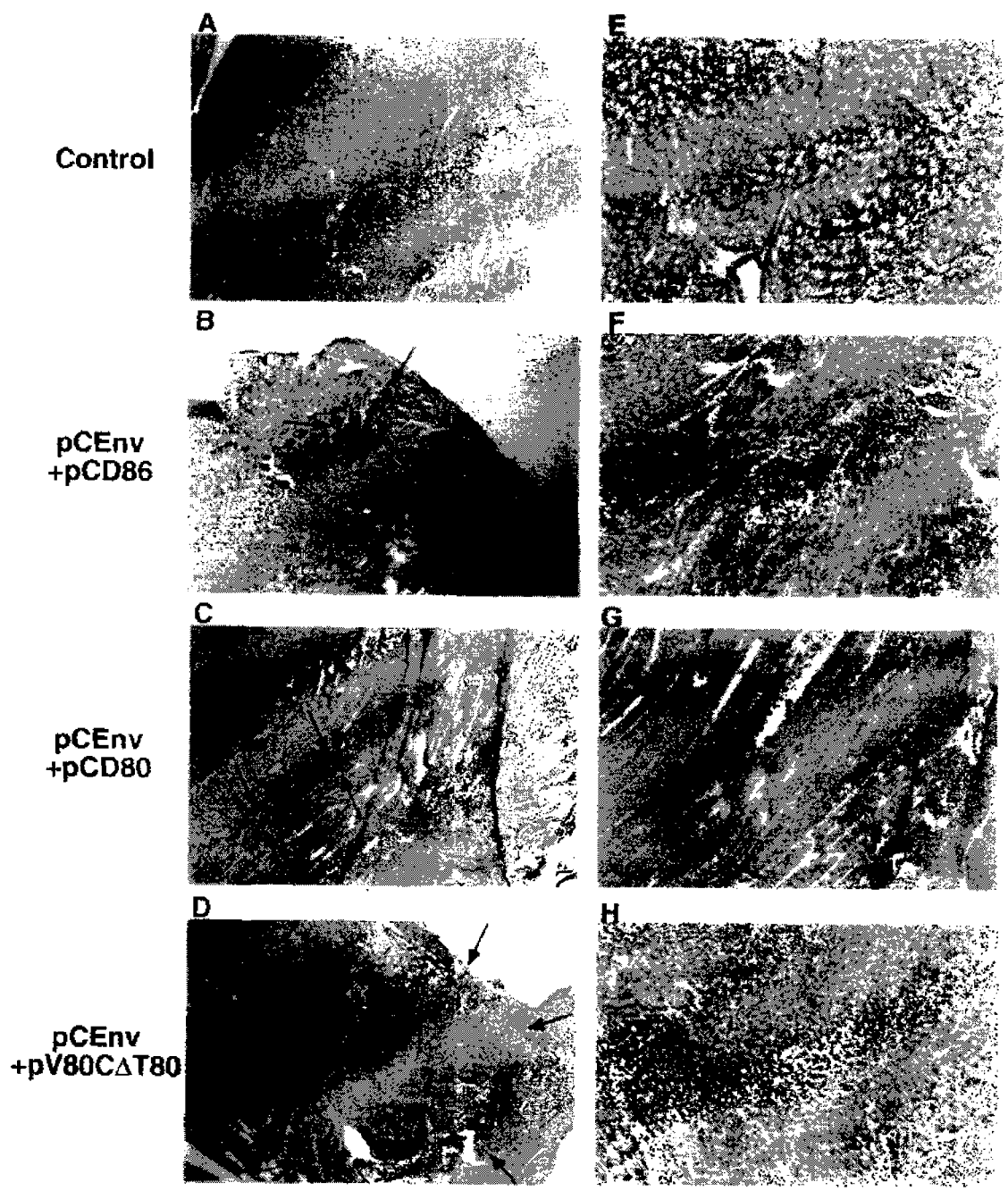
FIG. 5 are photographs from experiments described in the Example showing infiltration of lymphocytes into the muscle of mice immunized with constructs.

A markedly greater infiltration of lymphocytes into the muscle of mice immunized with pCEnv+pCD86 than in control or pCEnv+pCD80 immunized animals has been reported. The infiltrating cells included both CD4 and CD8' T cells. Thus, to further determine the ability of C-domain deleted CD80 molecules to interact with T cells, infiltration of cells into the muscle tissue after coinjection of mice with pcEnv plus pV80CΔT80 was investigate. As a control, animals injected with vector alone or a mixture of pcEnv plus pCD80 or pCD86 were used. Coinjection of mice with pCEnv+pCD86, but not pcEnv+pCD80 induced a dramatic infiltration of lymphocytes into the muscle tissue (FIG. 5). Normal animals developed virtually no infiltration. More importantly, infiltration was much greater in the muscle of mice coimmunized with DNA immunogen and pV80CΔT80. Therefore, the deletion of the C-domain changed the costimulatory properties of CD80 to resemble those of a wildtype of CD86.

CD80 and CD80 C-Domain Deleted Mutants have Different Binding Affinity to CTLA-4

As demonstrated above, communication of mice with DNA immunogen and pCD86 or pV80CΔT80 enhanced CTL activity, Th1 cytokine production, and infiltration of cells in the site of injection. In contrast, immunization with DNA immunogen and pCD80 did not have a similar effect. We postulate that the deletion of the C-domain of CD80 results in a molecule with decreased affinity for CTLA-4. This results in the ability to provide a potent negative signal to T cells. We used surface plasmon resonance to compare differences in CTLA-4 binding affinity between CD80 and the CD80 C-domain deletion mutant. Typically receptor (counterreceptor) molecules are immobilized to the sensor surface and different concentration of the counterreceptor (receptor) continuously flow through this sensor. Using this methodology it was shown that human soluble CTLA-4 bound to soluble CD80 with solution $K_D$ of 0.2-0.4 μM. Cells expressing the ligand of interest were immobilized on the surface of the. Cell immobilization allows maximum access of the cell surface CD-80 epitopes to the bulk of soluble CTLA-4-Ig with minimal conformational distortion of ligands. Lateral diffusion within the membrane bilayer allows for physiologic oligomerization of the CD80 ligands upon binding to CTLA-4. Using this approach, CTLA-4-Ig was demonstrated to specifically binds to RD cells, transfected with both the CD80 wildtype and CD80 C-domain deletion molecules. Importantly this binding was concentration dependent. After subtraction of the non-specific signal from the binding of the monoclonal antibodies affinities were calculated. Association of CTLA-4-Ig with the wildtype CD80 receptor is 5 times faster than with the mutant CD80 ($k_{on}$ parameter), while dissociation of CTLA-4/CD80 complex is 2.8 times slower for the wildtype receptor ($k_{off}$ parameter). Because of these differences in kinetics, the CTLA-4-Ig/CD80 wildtype interaction is 14 times stronger than with CD80 mutant as reflected in $K_D$. By definition $k_{off}$ and $k_{on}$ parameters measured by Biacore do not depend on the number of receptors, expressed at the cell surface. Thus, deletion of the constant region of CD80 receptor has a profound effect on the CD80-CTLA-4 interaction itself.

DISCUSSION

Current evidence indicates that one of the most important costimulatory pathways for T cell activation involves CD80 and CD86 expression on APC. These molecules interact with T cell surface receptors (CD28 or CTLA-4) and provide secondary signals important for proliferation and cytokine secretion. The critical costimulatory signal for T cell activation is provided through CD28 after binding to the B7 ligands. In contrast, CTLA-4 primarily induces an inhibitory signal. The evidence defining the functional roles of the CD80 and CD86 molecules is more complicated. It was demonstrated in several mainly in vitro models that both CD80 and CD86 have critical roles in the activation of T cells. However, expression of CD86 earlier than CD80 strongly suggesting that CD86 plays a more significant role in initiating T-cell immune responses. Differences between CD80 and CD86 can be inferred by data on the binding kinetics of costimulatory molecules with CD28 and CTLA-4. Recently, functional differences between CD80 and CD86 molecules have also been documented in many model systems including DNA immunization.

The CD86 molecule, but not CD80, is more important in providing of secondary signals to T cells following DNA vaccination of mice. However, CD80 as well as CD86 has been reported to enhance CTL responses when it was coexpressed with plasmid DNA encoding a minigene. This result is different than other reported results suggesting that free epitopes rather than natural antigens can behave uniquely. The similarity of the results from different groups are instructive, suggesting that expression of CD86 might be more important than CD80 in initiating and expanding in vivo cellular immune responses.

To further investigate the role of CD80 and CD86 molecules in T-cell activation, several chimeric and deletional mutant forms of CD80 and CD86 (Table 3) were constructed. These plasmids were coinjected in mice with an HIV-1/Env DNA immunogen and CTL activity as well as Th1 lymphokine production were determined. Chimeric pV80C86T86 as well as pCD86, but not pCD80 support the activation of T-cells (Table 4). This is significant since both the CD80 and CD86 V-domains can activate T-cells. These results also suggested that the C-domain and the cytoplasmic tail of CD86 can support T-cell activation. Of note, the opposite chimeric construction (pV86C80T80) did not enable the necessary costimulatory signal for antigen-specific T-cell stimulation.

This raised the possibility that the C-domain and/or cytoplasmic tail of CD80 may play an important inhibitory role in T cell activation. Deletional mutants of the B7 molecules which lacked the cytoplasmic tail or C-domains were then used. This allowed the direct assessment of the role of these molecular regions in T-cell activation or inhibition.

It was observed in vivo that the cytoplasmic tail of CD86 is absolutely necessary for anti-viral CTL responses and for Th1 cytokine production (Table 4). However, failure of the CD80 cytoplasmic tail deletion molecule (pV80C80TΔ) to induce T-cell activation did not allow the mapping of the inhibitory region of this molecule to the CD80 C-domain or cytoplasmic tail. This question was resolved by coimmunization of mice with the genes encoding the immunogen and the C-domain deleted CD80 molecule (FIGS. 1, 2A and 2B). A dramatic enhancement of T-cell activation in mice coinjected with pV80CΔT80 and pCEnv was observed. The cytoplasmic tail of CD80, like the cytoplasmic tail of CD86, appears to be involved in T cell activation and is not involved in the inhibition of T-cell activation. The cytoplasmic tail played an important role in both redistribution and oligomerization of this molecule on the surface of professional APC. Importantly it has been demonstrated also that activation of CD80 transfected cells with ionomycin and or PMA resulted in the association of a 30 kDa phosphoprotein with the CD80 cytoplasmic tail. Similar size of protein that was inducibly phosphorylated on tyrosine after CD80 cross-linking has been reported. Finally it was reported that the triggering of CD86 molecules activates expression of new immunoglobulin genes in the B-cells. These results strongly indicate that the B7 molecules may provide a direct signal back to the APC. Based upon these results as well as our data presented above we further hypothesized that B7 could provide a direct signal to APC and in turn induce the secretion/expression of certain molecules (cytokines, lymphokines, chemokines, etc), which are important for activation or inhibition of cellular immune responses. Examples of such molecules could include IL-1α, IL-1β, IL-12 and TNF cytokines, which are produced by professional APC and play an important role in immune activation. In fact recently, these cytokines were directly demonstrated to modulate humoral and cellular anti-viral immune responses during DNA coimmunization.

Another important observation was that the C-domain of CD80, but not that of CD86, somehow inhibited costimulation of T-cells. At least C-domain deleted mutants could significantly increase T-cell activation in our experiments (FIGS. 1, 2A and 2B), whereas the wildtype molecule could not (Table 4). Recent studies demonstrated a mechanism of T-cell inactivation is mediated through CTLA-4 interactions with a chain of the TCR. Accordingly, our experiments suggest that both V- and C-domains of CD80 may be essential for CTLA-4 binding and the subsequent inhibitory signal sent via the TCR overrides simultaneously transmitted CD28 activation signals. To directly test this hypothesis animals were coimmunized with a DNA immunogen and a combination of CD80 and CD86 molecules. Coinjection of pCD80 with pCD86 along with the DNA immunogen eliminated the strong anti-viral $CD8^+$ CTL response normally seen after pCD86 costimulation (FIGS. 3, 4). Importantly the C-domain deleted form of CD80 molecule did not generate this inhibitory signal (FIG. 3). Therefore, molecules expressing both V- and C-domains of CD80 not only prevented T-cell activation, probably through preferential binding to CTLA-4, but also could overcome the positive signal provided by triggering of CD28 ligand by V-domains of both CD80 and CD86 molecules. In fact there has been a demonstrated predominance of CTLA-4 signaling over CD28 in which CD28 activation pathways are directly inhibited as a result of simultaneous CTLA-4 crosslinking Since the CD80 molecule can bind to both CD28 and CTLA-4 there must be important structural differences that shift the equilibrium in the favor of the CTLA-4 inhibition pathway over CD28 activation pathway. Surface plasmon resonance analysis measured a fourteen-fold increase in binding between CTLA4 and CD80 when the C-domain. It is more likely that this difference is actually higher, because a multivalent interaction of CTLA-4 and B7 is likely to occur. The rate of dissociation of the individual component of CTLA-4 with CD80 is similar to the monomeric dissociation. However, since the CD80 will still be held by the second CTLA-4 interaction, the observed rate of dissociation will be much slower, thus forming a more stable CTLA-4/CD80 complex. Accordingly if the difference in binding avidity of membrane CTLA-4 to membrane CD80 or membrane CD80 C-domain deleted mutants is calculated, it will be a multiple of 14, The data clearly indicates that the C-domain of CD80 not only prevents T-cell activation, but also alters structure function relationships of this molecule with CTLA-4.

The expression of genes encoding the C-domain deletion mutant of CD80 induced not only T-cell activation, but also huge infiltration into the muscle of experimental animals. This infiltration was even greater than the infiltration observed after pCD86 and pCEnv coexpression (FIG. 5). Recently, it was reported the APC activity of human muscle cells in vitro. After activation with cytokines, human myoblasts can express costimulatory molecules and can function as professional MHC class II restricted APC, In addition, in vivo effect of muscle cells in T-cell activation is demonstrated. Mouse muscle cells have been converted to MHC class I restricted APC by the expression of CD86, but not CD80 molecules. The data reported herein can be interpreted as showing that DNA immunization with pcEnv induces a small infiltration of immunocompetent cells into the site of injection. These infiltrating T cells can be activated by transfected muscle cells expressing MHC class I molecules and foreign peptide as well as CD86 molecules. Activated T-cells in turn might produce chemokines and attract more T-cells to the site of inflammation. Accordingly, a huge infiltration is observed in the muscle tissue in case of coimmunization with pcEnv plus pCD86 (FIG. 5). The same mechanism will apply after coimmunization with DNA immunogen and pV80CΔT80. However, coadministration of pCD80 and pcEnv induced only small infiltration in the muscle tissue of experimental animals. If one remembers that CD80 molecule can bind to both CD28 and CTLA-4 there must be forces that shift the equilibrium in the favor of the CTLA-4 inhibition pathway over CD28 activation pathway. The presence of the C-domain of CD80 in muscle cells transfected with wildtype CD80 seems to have a very early inhibitory effect on the infiltration and/or proliferation of activated lymphocytes in this tissue and may reflect a preferential binding to and signaling through CTLA-4. Therefore T-cells in the site of injection will not produce chemokines and will not induce migration of other lymphocytes in the area of immunization (FIG. 5). Importantly, whether one of the costimulatory molecules preferentially functions by interaction with CTLA-4 as opposed to CD28 has not been evaluated and the structural basis for this interaction is still unclear.

Earlier, a number of studies have reported the results of site directed mutagenesis experiments that investigated the structure function relationships of B7 and CD28/CTLA-4 molecules. Collectively these studies implicated more than 20 residues on both V and C-domains of CD80 critical for CTLA-4 binding. However, the exact region important for interaction of CD80 molecule to CTLA-4 and CD28 is not defined. Spleen and lymph nodes of mice has been shown to have an alternatively spliced form of CD80 that lacks C-domain. This naturally synthesized IgV molecule binds to CD28=Ig very well (comparable to CD80), although its binding to CTLA-4 was suppressed significantly. At least one group also demonstrated that deletion of the C-domain of CD80 molecule had a greater effect on binding to CTLA-4=Ig, than CD28=Ig. Importantly, IgV-like region of CD80 could activate proliferation of activated T-cells in vitro. In vivo data showing effective costimulation provided by the CD80 C-domain deletion molecule support these results. Any explanations for the inhibitory nature of costimulatory molecules expressing the C-domain of CD80 should consider the increased avidity of CD80 binding by CTLA-4 as compared to CD28. Recent measurements indicate that binding avidity of CD80 to dimeric CTLA-4 is much higher than to dimeric CD28. Importantly, dimeric CTLA-4 binds to CD80 with greater avidity than to CD86. This greater binding strength may explain why the CTLA-4 induced inhibitory signal predominates in this experimental system. In order to further reveal important differences in CTLA-4 binding region of CD80 and CD86 we constructed three-dimensional models of both C-domains.

Correlation of mutational studies with three-dimensional models of the C-domain of CD80 provide some insight into receptor binding. Both CD80 and CD86 display sequence homology with Ig folds suggesting that both adopt similar conformations (Table 6). Consequently, most mutational analysis have focused on changing conserved residues between human and mouse CD80 and those conserved between CD80 and CD86. Several conserved residues in the C domain of CD80 appear to be critical for binding to CTLA-4=Ig (Table 6).

A model has established that Q157, D158, E162 and L163 spatially cluster in surface accessible positions near the amino-terminal end of the domain in the loop between strands D and E and at the beginning of strand E. Other residues (F108, P111, and I113) mapped to strand A (see Table 6). The second model constructed on the basis of mutational analysis also demonstrates a critical role for P135 and P137 in the B-C loop as well as Q157, D158 and P159 in the D-E loop for binding CTLA4. Collectively the residues important for receptor binding are mapped to the ABCED face of the IgC domain.

Figure 6:
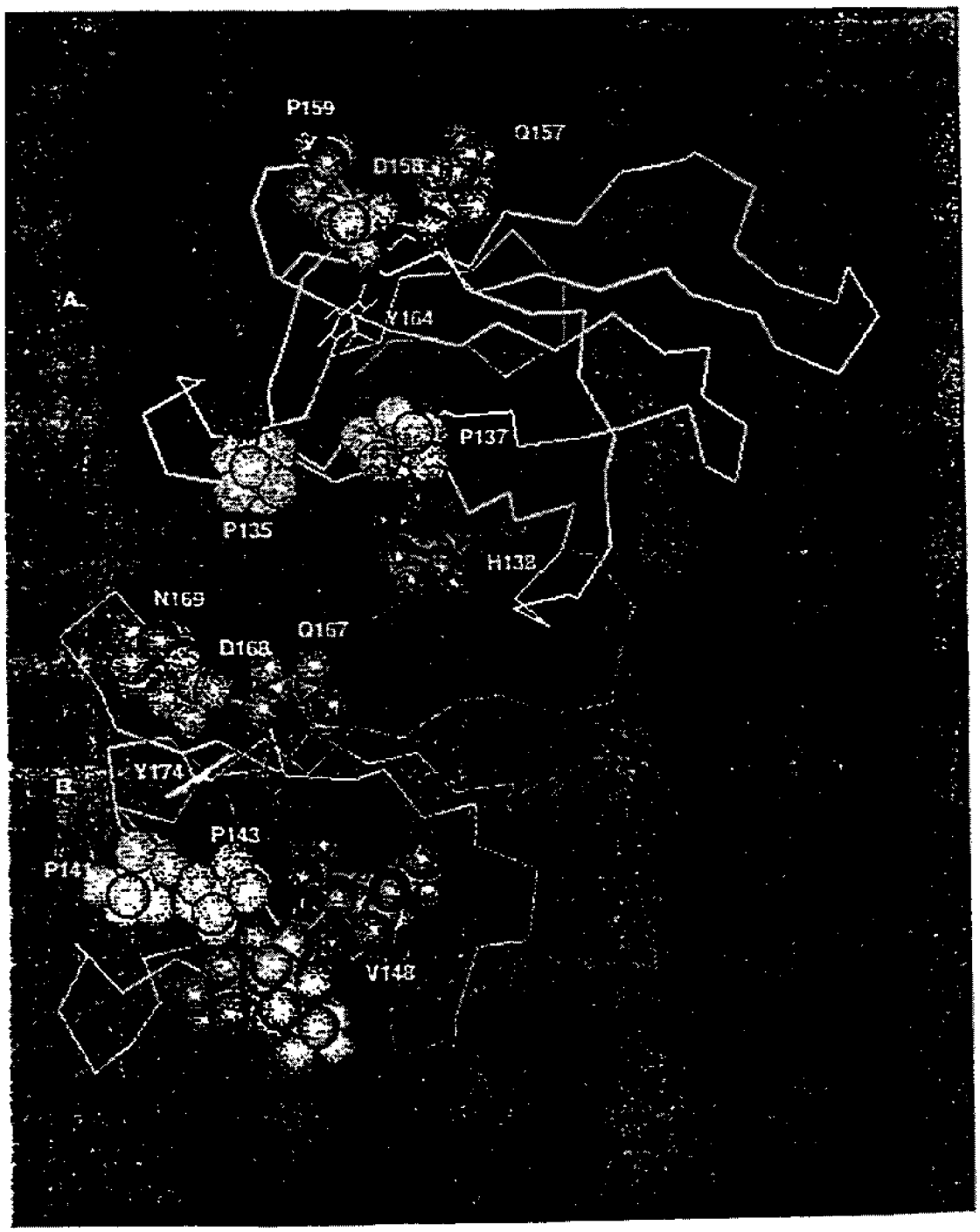
FIG. 6 is a graphic representation of the CD80 molecule.

FIG. 6 shows Cα traces of CD80 molecule with CTLA4 binding region residues represented as CPK renderings where B-C loop amino acids P135 and P136 and D-E loop residues Q157, D158, P159 are shown. In the corresponding model of CD86 there is a 4 residues insertion 144-147 (KKMS) shown in italic in Table 6 and in FIG. 6. This insertion in CD86 changes the conformation of the B-C loop in this molecule in comparison to CD80, so that the binding region becomes significantly smaller. Because of that insertion, the distance between P159 and P135 decreases from 16 Å in CD80 to 12 Å for the corresponding residues of CD86. In addition, the distance between Q157 and P137 decreases from 13 Å in CD80 to 10 Å for the corresponding residues of CD86. Therefore, this insertion changes the conformation of the B-C loop of the CD86 molecule in comparison to CD80 so that the total surface area of the CTLA-4 binding in CD86 molecule is significantly smaller than the same region of CD80 (Compare FIG. 6). Thus, modeling of CD80 and CD86 suggests that conformation of B-C loop is different in these molecules and that KKMS insert in CD86 may play an important role in decreasing of the avidity of binding to CTLA-4 and consequently can decrease the inhibitory signal being targeted to the T-cells.

In summary, discrepancies regarding the binding/functional sites of V and C-domains of CD80 and to a lesser extent of CD86 molecules to CTLA-4 and/or CD28 ligands may be explained by different antigens and experimental systems used in different laboratories. For example many results with T-cell costimulation were obtained with anti-CD3 monoclonal antibodies (1-st signal) and soluble forms of B7 (CD80=Ig, CD86=Ig) molecules (2-nd signal). This model generated very important data. However, recent published results demonstrated that only cells expressing oligomeric forms of costimulatory molecules can drive T-cell activation. On the other hand, even usage of CD80 and CD86 transfected cells for costimulation of T cell may not be considered as an optimal model. It was reported that CTLA-4 interacts with TCRζ after triggering with anti-CD3 and membrane-bound CD80 molecules. These results suggest that proper model probably should include interaction of APC, expressing MHC class I/II, and CD80/CD86 with T-cells, expressing TCR and CD28/CTLA-4. Accordingly, in vivo physiological conditions for APC and T-cell interaction may be more appropriate for uncovering the mechanism/s of T-cell costimulation. Using this model system, functional differences between CD80 and CD86 as well as between V- and C-domains of CD80 molecule has been demonstrated.

The current studies provide important information for the development of new approaches for the regulation of T-cell immune responses. Specifically, a form of the B7 ligand can be provided to for example include both V- and C-domains that could inactivate an ongoing human immune response probably by preferentially triggering to CTLA-4 molecules, expressed on antigen-specific T-cells. Such a construct may have important applications for transplantation tolerance or in the treatment of autoimmune disease. Conversely, more effective tumor vaccination may result from the coimmunization provided through V-domain of CD80 with a decreased ability to inhibit of T-cell activation. Additionally, vaccines that are targeted towards improved cellular immunity may be provided using molecular adjuvants described herein.

TABLE 1

| | |
|---|---|
| Picornavirus Family | Rhinoviruses: (Medical) responsible for ~50% cases of the common cold. |
| Genera: | Etheroviruses: (Medical) includes polioviruses, coxsackieviruses, echoviruses, and human enteroviruses such as hepatitis A virus. |
| | Apthoviruses: (Veterinary) these are the foot and mouth disease viruses. |
| Target antigens: | VP1, VP2, VP3, VP4, VPG |
| Calcivirus Family | Norwalk Group of Viruses: (Medical) these viruses are |
| Genera: | an important causative agent of epidemic gastroenteritis. |

TABLE 1-continued

| | |
|---|---|
| Togavirus Family Genera: | Alphaviruses: (Medical and Veterinary) examples include Senilis viruses, RossRiver virus and Eastern & Western Equine encephalitis. |
| | Reovirus: (Medical) Rubella virus. |
| Flariviridue Family | Examples include: (Medical) dengue, yellow fever, Japanese encephalitis, St. Louis encephalitis and tick borne encephalitis viruses. Hepatitis C Virus: (Medical) these viruses are not placed in a family yet but are believed to be either a togavirus or a flavivirus. Most similarity is with togavirus family. |
| Coronavirus Family: (Medical and Veterinary) | Infectious bronchitis virus (poultry) Porcine transmissible gastroenteric virus (pig) Porcine hemaglutinating encephalomyelitis virus (pig) Feline infectious peritonitis virus (cats) Feline enteric coronavirus (cat) Canine coronavirus (dog) The human respiratory coronaviruses cause ~40 cases of common cold. EX. 224E, OC43 Note - coronaviruses may cause non-A, B or C hepatitis |
| Target antigens: | E1 - also called M or matrix protein E2 - also called S or Spike protein E3 - also called BE or hemagglutin-elterose glycoprotein (not present in all coronaviruses) N - nucleocapsid |
| Rhabdovirus Family Genera: | Vesiliovirus Lyssavirus: (medical and veterinary) rabies |
| Target antigen: | G protein N protein |
| Filoviridue Family: (Medical) | Hemorrhagic fever viruses such as Marburg and Ebola virus |
| Paramyxovirus Family: Genera: | Paramyxovirus: (Medical and Veterinary) Mumps virus, New Castle disease virus (important pathogen in chickens) Morbillivirus: (Medical and Veterinary) Measles, canine distemper Pneuminvirus: (Medical and Veterinary) Respiratory syncytial virus |
| Orthomyxovirus Family (Medical) | The Influenza virus |
| Bungavirus Family Genera: | Bungavirus: (Medical) California encephalitis, LA Crosse Phlebovirus: (Medical) Rift Valley Fever Hantavirus: Puremala is a hemahagin fever virus Nairvirus (Veterinary) Nairobi sheep disease Also many unassigned bungaviruses |
| Arenavirus Family (Medical) | LCM, Lassi fever virus |
| Reovirus Family Genera: | Reovirus: a possible human pathogen Rotavirus: acute gastroenteritis in children Orbiviruses: (Medical and Veterinary) Colorado Tick fever, Lebombo (humans) equine encephalosis, blue tongue |
| Retrovirus Family | |
| Sub-Family: | Oncorivirinal: (Veterinary) (Medical) feline leukemia virus, HTLVI and HTLVII Lentivirinal: (Medical and Veterinary) HIV, feline immunodeficiency virus, equine infections, anemia virus Spumavirinal |
| Papovavirus Family | |
| Sub-Family: | Polyomaviruses: (Medical) BKU and JCU viruses |
| Sub-Family: | Papillomavirus: (Medical) many viral types associated with cancers or malignant progression of papilloma. |
| Adenovirus (Medical) | EX AD7, ARD., O.B. - cause respiratory disease - some adenoviruses such as 275 cause enteritis |
| Parvovirus Family (Veterinary) | Feline parvovirus: causes feline enteritis Feline panleucopeniavirus Canine parvovirus Porcine parvovirus |
| Herpesvirus Family | |
| Sub-Family: Genera: | alphaherpesviridue Simplexvirus (Medical) HSVI, HSVII Varicellovinis: (Medical - Veterinary) pseudorabies - varicella zoster |
| Sub-Family - Genera: | betaherpesviridue Cytomegalovirus (Medical) HCMV Muromegalovirus |

TABLE 1-continued

| | |
|---|---|
| Sub-Family: | Gammaherpesviridue |
| Genera: | Lymphocryptovirus (Medical) |
| | EBV - (Burkitts lympho) |
| | Rhadinovirus |
| Poxvirus Family | |
| Sub-Family: | Chordopoxviridue (Medical - Veterinary) |
| Genera: | Variola. (Smallpox) |
| | Vaccinia (Cowpox) |
| | Parapoxivirus - Veterinary |
| | Auipoxvirus - Veterinary |
| | Capripoxvirus |
| | Leporipoxvirus |
| | Suipoxvirus |
| Sub-Family: | Entemopoxviridue |
| Hepadnavirus Family | Hepatitis B virus |
| Unclassified | Hepatitis delta virus |

TABLE 2

| | |
|---|---|
| Bacterial pathogens | Pathogenic gram-positive cocci include: pneumococcal; staphylococcal; and streptococcal. Pathogenic gram-negative cocci include: meningococcal; and gonococcal. Pathogenic enteric gram-negative bacilli include: enterobacteriaceae; *pseudomonas*, acinetobacteria and *eikenella*, melioidosis; *salmonella*; shigellosis; hemophilus; chancroid; brucellosis; tularemia; *yersinia* (*pasteurella*); *streptobacillus moniliformis* and *spirillum*; *listeria monocytogenes*; *erysipelothrix rhusiopathiae*; diphtheria, cholera, anthrax; donovanosis (granuloma inguinale); and bartonellosis. Pathogenic anaerobic bacteria include: tetanus; botulism; other clostridia; *tuberculosis*; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma, and chromomycosis; and dermatophytosis. Rickettsial infections include rickettsial and rickettsioses. Examples of mycoplasma and chlarnydial infections include: *mycoplasma pneumoniae*; lymphogranuloma venereum; psittacosis; and perinatal chlarnydial infections. |
| Pathogenic eukaryotes | Pathogenic protozoans and helminths and infections thereby include: amebiasis; malaria; leishmaniasis; trypanosomiasis; toxoplasmosis; *pneumocystis carinii*; babesiosis; giardiasis; trichinosis; filariasis; schistosomiasis; nematodes; trematodes or flukes; and cestode (tapeworm) infections. |

TABLE 3

Expression efficiency of constructs encoding wildtype, chimeric, or truncated forms of CD80 and CD86 molecules detected by FACS assay.

| Plasmids | Schematic Representation of Ig Domains * | Description of encoded protein | FI** |
|---|---|---|---|
| Vector control | | No Insert | 2.5 |
| pCD80 | → ▬ | Wildtype CD80 | 8.5 |
| pV80CΔT80 | → ▬ | Truncated CD80, C domain deletion | 6.33 |
| pV80C86T86 | → ▬[C][T] | Chimeric, V domain of CD 86 substituted by V domain of CD80 | 5.9 |
| pV80C80TΔ | → ▬ | Truncated CD80, cytoplasmic (T) domain deletion | 5.8 |
| pCD86 | → [V][C][T] | Wildtype CD86 | 5.99 |
| pV86CΔT86 | → [V][T] | Truncated CD86, C domain deletion | 7.1 |

TABLE 3-continued

Expression efficiency of constructs encoding wildtype, chimeric, or truncated forms of CD80 and CD86 molecules detected by FACS assay.

| Plasmids | Schematic Representation of Ig Domains * | Description of encoded protein | FI** |
|---|---|---|---|
| pV86C80T80 | [V ■] | Chimeric, V domain of CD 80 substituted by V domain of CD86 | 7.4 |
| pV86C86TΔ | [V C] | Truncated CD86, cytoplasmic (T) domain deletion | 11.16 |

* Boxes represent V, C and T (cytoplasmic tail) domains of CD80 (shaded) and CD86 (open) molecules (transmembrane sequence was not removed.
**Rhabdomyosarcoma cells were cotransfected with experimental or control plasmids and a construct encoding the green fluorescence protein (GFP). Fluorescence Intensity (FI) of cells expressing B7 molecules (red mean channel) was detected in the population of cells expressing GFP.

TABLE 4

Cellular immune responses (CTL and Th1 cytokine production) in mice coimmunized with plasmids, encoding viral antigen and different forms of B7 molecules.

| Mice immunized with the following plasmids | * Anti-viral CTL (%) at different E:T ratio | | | * Th1 cytokines (pg/ml) | |
|---|---|---|---|---|---|
| | 100:1 | 50:1 | 25:1 | γIFN | IL-12 |
| Naïve | 1.1 | 2.5 | 4.3 | 34.50 | 16.80 |
| pcEnv | 13.3 | 12.8 | 13.7 | 46.50 | 31.37 |
| pcEnv + pcD80 | 16.6 | 12.5 | 11.3 | 36.32 | 36.99 |
| pcEnv + pcD86 | 47.7 | 34.8 | 24.7 | 334.54 | 71.86 |
| pcEnv + pV80C86T86 | 42.8 | 36.2 | 28.5 | 500.37 | 90.32 |
| pcEnv + pV86C80T80 | 16.4 | 17.1 | 13.4 | 50.93 | 26.42 |
| pcEnv + pV80C80TΔ | 14.5 | 8.6 | 5.1 | 41.25 | 21.87 |
| pcEnv + pV86C86TΔ | 11.0 | 8.7 | 10.6 | 38.91 | 31.86 |

* Two weeks after the last immunization spleens were collected and CTL and Th1 cytokine assays were performed as described in Materials and Methods. These experiments have been repeated three (for detection of CTL) and two (for detection of cytokines) times with similar results.

TABLE 5

Binding parameters for CTLA-4/CD80 interaction estimated from fits to a Langmuir model

| CD80 type | $k_{on}$ (1/Ms) | $k_{off}$ (1/s) | $K_D$ (M) |
|---|---|---|---|
| Wildtype | $3.99 \times 10^3$ | $2.00 \times 10^{-4}$ | $5.02 \times 10^{-10}$ |
| CD80 | | | |
| C-domain deleted | $7.86 \times 10^4$ | $5.53 \times 10^{-4}$ | $7.04 \times 10^{-9}$ |
| CD80 | | | |

TABLE 6

Sequence alignment of C-domains of human CD80 and CD86.

| Human CD80 and CD86 | Sequence Alignment | AA # |
|---|---|---|
| Human CD80 | KADFPTPSISDFE.IPTSNIRRIICSTSGGFPEP | 137 |
| Human CD86 | LANFSQPEIVPISNITENVYINLTCSSIHGYPEP | 143 |
| | Strand A        Strand B | |
| Human CD80 | ....HLSWLE                    HLSWLE.... | 143 |
| Human CD86 | *KKMS* VLLRTK        OR        KKMSV*LLRTK* | 153 |
| | Strand C                Strand C | |
| Human CD80 | NGEELNAINTTVSQDPETELYAVSSKLDFNM...TT | 176 |
| Human CD86 | NSTIEYDGIMQKSQDNVTELYDVSISLSVSFPDVTS | 189 |
| | Strand D        Strand E | |
| Human CD80 | NHSFMCLIKYGHLRVNQTFNWNTT | 200 |
| Human CD86 | NMTIFCILETDKTRLLSSPFSIEL | 213 |
| | Strand F        Strand G | |

*Alignments were done using CLUSTALW (Thompson, 1994) and then adjusted manually. Residues at the end of each row are numbered from their respective N-terminus. Residues of CD80 critical for binding T cell surface receptor CTLA-4 according to literature (Ellis, 1996; Fargeas, 1995; Guo, 1995; Guo, 1998; Peach, 1995) are shown in bold face. Two presumable variants of four amino acids insert in CD86 are shown in italic and more likely could disturb binding to CTLA-4 (see details in discussion). Highlighted beta strands in both CD80 and CD86 based on the crystal structure of sB7-1 (Ikemizu, 2000).

The invention claimed is:

1. A method immunizing an individual against an immunogen comprising administering a composition comprising
   a) a nucleic acid sequence comprising a human CD80 mutant protein coding sequence operably linked to regulatory elements, wherein said human CD80 mutant protein coding sequence encodes a human CD80 mutant protein that comprises at least one of 80V, 80tm and 80ct and is free of all or part of the CD80 C region; wherein said CD80 mutant that is free of all or part of the CD80 C region comprises either 80V or 86ct or both and optionally comprises one or more of 86C, 80tm, 86tm, 80ct and 86ct wherein: 80V is the variable domain of human CD80; 86V is the variable domain of a human CD86; 86C is the C domain of human CD86; 80tm is the transmembrane region of human CD80; 86tm is the transmembrane region of a human CD86; 80ct is the cytoplasmic tail of human CD80; 86ct is the cytoplasmic tail of human CD86; wherein said human CD80 mutant protein possesses costimulatory activity of wild type CD80 and does not provide the negative signal associated with wild type human CD80 C region interactions with human CTLA4, and
   b) a nucleic acid sequence comprising a coding sequence operably linked to regulatory elements, wherein said coding sequence that encodes said immunogen.

2. The method of claim 1 wherein said immunogen is an allergen.

3. The method of claim 1 wherein said immunogen is a pathogen antigen.

4. The method of claim 1 wherein said nucleic acid sequence that encodes a human CD80 mutant protein and said nucleic acid sequence that encodes the immunogen are part of same nucleic acid molecule.

5. The method of claim 4 wherein said nucleic acid molecule is a plasmid.

6. The method of claim 1 wherein said nucleic acid sequence that encodes a human CD80 mutant protein is part of a first nucleic acid molecule and said nucleic acid sequence that encodes the immunogen are part of a second nucleic acid molecule.

7. The method of claim 1 wherein said first nucleic acid molecule is a plasmid and said second nucleic acid molecule is a plasmid.

8. The method of claim 1 wherein said human CD80 mutant protein comprises part of human CD80 C region.

9. The method of claim 8 wherein said nucleic acid sequence that encodes a human CD80 mutant protein is part of one nucleic acid molecule and said nucleic acid sequence that encodes the immunogen are part of the same nucleic acid molecule.

10. The method of claim 9 wherein the nucleic acid molecule is a plasmid.

11. The method of claim 8 wherein said nucleic acid sequence that encodes a human CD80 mutant protein that comprises part of human CD80 C region is part of a first nucleic acid molecule and said nucleic acid sequence that encodes the immunogen are part of the second nucleic acid molecule.

12. The method of claim 11 wherein said first nucleic acid molecule is a plasmid and said second nucleic acid molecule is a plasmid.

13. The method of claim 1 wherein said human CD80 mutant protein comprises a human CD80 V region, a functional human CD80 μm and a human CD80 ct region, and is free of a functional C region by the absence of all or part of the a human CD80 C region.

14. The method of claim 13 wherein said nucleic acid sequence that encodes a human CD80 mutant protein is part of one nucleic acid molecule and said nucleic acid sequence that encodes the immunogen are part of the same nucleic acid molecule.

15. The method of claim 14 wherein the nucleic acid molecule is a plasmid.

16. The method of claim 13 wherein said nucleic acid sequence that encodes a human CD80 mutant protein is part of a first nucleic acid molecule and said nucleic acid sequence that encodes the immunogen are part of the second nucleic acid molecule.

17. The method of claim 16 wherein said first nucleic acid molecule is a plasmid and said second nucleic acid molecule is a plasmid.

18. The method of claim 1 wherein the composition is administered into skin tissue.

19. The method of claim 1 wherein the composition is administered intramuscularly.

20. The method of claim 13 wherein the composition is administered into skin tissue.

21. The method of claim 13 wherein the composition is administered intramuscularly.

* * * * *

SEQUENCE LISTING

<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 1
ctgcttgctc aactctacgt c                                              21

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 2
ctgaagttag ctttgactga taacg                                          25

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 3
gcaatagcat cacaaatttc a                                              21

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
cagtcaaagc taacttcagt caacc                                          25

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
gggaagtcag caagcactga cagttc                                         26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 6
tcagtgcttg ctgacttccc tacacc                                    26

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7
tcttgcttgg ctttgactga taacgtcac                                 29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 8
tcagtcaaag ccaagcaaga gcattttcc                                 29

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9
tcctcaagct caagcactga cagttc                                    26

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
tcagtgcttg agcttgagga ccc                                       23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11
tctggatcct catcttgggg ca                                        22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 12
tctggatcct catttccata g                                         21

<210> SEQ ID NO 13
<211> LENGTH: 33
<212> TYPE: PRT
<213> ORGANISM: Homo sapiens

<400> SEQUENCE: 13

Lys Ala Asp Phe Pro Thr Pro Ser Ile Ser Asp Phe Glu Ile Pro Thr
1               5                   10                  15
Ser Asn Ile Arg Arg Ile Ile Cys Ser Thr Ser Gly Gly Phe Pro Glu
            20                  25                  30
Pro

<210> SEQ ID NO 14
<211> LENGTH: 34
<212> TYPE: PRT
<213> ORGANISM: Homo sapiens

<400> SEQUENCE: 14

Leu Ala Asn Phe Ser Gln Pro Glu Ile Val Pro Ile Ser Asn Ile Thr
1               5                   10                  15
Glu Asn Val Tyr Ile Asn Leu Thr Cys Ser Ser Ile His Gly Tyr Pro
            20                  25                  30
Glu Pro

<210> SEQ ID NO 15
<211> LENGTH: 6
<212> TYPE: PRT
<213> ORGANISM: Homo sapiens

<400> SEQUENCE: 15

His Leu Ser Trp Leu Glu
1               5

<210> SEQ ID NO 16
<211> LENGTH: 10
<212> TYPE: PRT
<213> ORGANISM: Homo sapiens

<400> SEQUENCE: 16

Lys Lys Met Ser Val Leu Leu Arg Thr Lys
1               5                   10

<210> SEQ ID NO 17
<211> LENGTH: 33
<212> TYPE: PRT
<213> ORGANISM: Homo sapiens

<400> SEQUENCE: 17

Asn Gly Glu Glu Leu Asn Ala Ile Asn Thr Thr Val Ser Gln Asp Pro
1               5                   10                  15
Glu Thr Glu Leu Tyr Ala Val Ser Ser Lys Leu Asp Phe Asn Met Thr
            20                  25                  30
Thr

<210> SEQ ID NO 18
<211> LENGTH: 36
<212> TYPE: PRT
<213> ORGANISM: Homo sapiens

<400> SEQUENCE: 18

Asn Ser Thr Ile Glu Tyr Asp Gly Ile Met Gln Lys Ser Gln Asp Asn
1               5                   10                  15

```
Val Thr Glu Leu Tyr Asp Val Ser Ile Ser Leu Ser Val Ser Phe Pro
            20                  25                  30

Asp Val Thr Ser
        35

<210> SEQ ID NO 19
<211> LENGTH: 24
<212> TYPE: PRT
<213> ORGANISM: Homo sapiens

<400> SEQUENCE: 19

Asn His Ser Phe Met Cys Leu Ile Lys Tyr Gly His Leu Arg Val Asn
1               5                   10                  15

Gln Thr Phe Asn Trp Asn Thr Thr
            20

<210> SEQ ID NO 20
<211> LENGTH: 24
<212> TYPE: PRT
<213> ORGANISM: Homo sapiens

<400> SEQUENCE: 20

Asn Met Thr Ile Phe Cys Ile Leu Glu Thr Asp Lys Thr Arg Leu Leu
1               5                   10                  15

Ser Ser Pro Phe Ser Ile Glu Leu
            20
```